(12) United States Patent
Ruchelman et al.

(10) Patent No.: US 12,049,470 B2
(45) Date of Patent: Jul. 30, 2024

(54) MK2 INHIBITORS, THE SYNTHESIS THEREOF, AND INTERMEDIATES THERETO

(71) Applicant: Celgene Corporation, Summit, NJ (US)

(72) Inventors: Alexander L. Ruchelman, Cream Ridge, NJ (US); John R. Coombs, New Brunswick, NJ (US); Keming Zhu, New Brunswick, NJ (US); Daniel Lim, Summit, NJ (US); Candice Lee Joe, New Brunswick, NJ (US); David T. George, New Brunswick, NJ (US); Bin Zheng, Kendall Park, NJ (US); Dong Lin, Monmouth Junction, NJ (US)

(73) Assignee: Celgene Corporation, Summit, NJ (US)

( * ) Notice: Subject to any disclaimer, the term of this patent is extended or adjusted under 35 U.S.C. 154(b) by 6 days.

(21) Appl. No.: 17/587,555

(22) Filed: Jan. 28, 2022

(65) Prior Publication Data
US 2022/0259222 A1    Aug. 18, 2022

Related U.S. Application Data

(60) Provisional application No. 63/144,361, filed on Feb. 1, 2021.

(51) Int. Cl.
| | |
|---|---|
| *C07D 215/227* | (2006.01) |
| *C07C 255/50* | (2006.01) |
| *C07D 215/58* | (2006.01) |
| *C07D 495/04* | (2006.01) |
| *C07D 495/14* | (2006.01) |

(52) U.S. Cl.
CPC .......... *C07D 495/14* (2013.01); *C07C 255/50* (2013.01); *C07D 215/58* (2013.01); *C07D 495/04* (2013.01)

(58) Field of Classification Search
CPC ................................................ C07D 215/227
See application file for complete search history.

(56) References Cited

U.S. PATENT DOCUMENTS

| | | |
|---|---|---|
| 7,838,674 B2 | 11/2010 | Schlapbach et al. |
| 9,458,175 B2 | 10/2016 | Alexander et al. |
| 9,790,235 B2 | 10/2017 | Alexander et al. |
| 10,138,256 B2 | 11/2018 | Alexander et al. |
| 10,253,040 B1 | 4/2019 | Alexander et al. |
| 10,577,380 B2 | 3/2020 | Alexander et al. |
| 10,882,867 B2 | 1/2021 | Han et al. |
| 10,894,796 B2 | 1/2021 | Feigelson et al. |
| 11,098,057 B2 | 8/2021 | Malona et al. |
| 11,124,525 B2 | 9/2021 | Guo et al. |
| 11,230,551 B2 | 1/2022 | Malona et al. |
| 11,584,757 B2 | 2/2023 | Alexander et al. |
| 11,629,153 B2 | 4/2023 | Han et al. |
| 11,655,257 B2 | 5/2023 | Feigelson et al. |
| 2009/0156557 A1 | 6/2009 | Brown et al. |
| 2012/0022030 A1 | 1/2012 | Schlapbach et al. |
| 2013/0137708 A1 | 5/2013 | Garske et al. |
| 2014/0018343 A1 | 1/2014 | Romero et al. |
| 2021/0053984 A1 | 2/2021 | Alexander et al. |
| 2021/0139501 A1 | 5/2021 | Feigelson et al. |
| 2021/0198276 A1 | 7/2021 | Han et al. |
| 2022/0064183 A1 | 3/2022 | Guo et al. |
| 2022/0251105 A1 | 8/2022 | Ramirez-Valle |

FOREIGN PATENT DOCUMENTS

| | | | |
|---|---|---|---|
| CN | 102753179 A | 10/2012 | |
| WO | WO-2004/058762 A1 | 7/2004 | |
| WO | WO-2009/010488 A1 | 1/2009 | |
| WO | WO-2012/003498 A1 | 1/2012 | |
| WO | WO-2012/056372 A1 | 5/2012 | |
| WO | WO-2012/137181 A1 | 10/2012 | |
| WO | WO-2012/140243 A1 | 10/2012 | |
| WO | WO-2013/146963 A1 | 10/2013 | |
| WO | WO-2014/003098 A1 | 1/2014 | |
| WO | WO-2014/008992 A1 | 1/2014 | |
| WO | WO-2014/050779 A1 | 4/2014 | |
| WO | WO-2014/149164 A1 | 9/2014 | |
| WO | WO-2015/128884 A1 | 9/2015 | |
| WO | WO-2016/044463 A2 | 3/2016 | |
| WO | WO-2018/170199 A1 | 9/2018 | |
| WO | WO-2018/170200 A1 | 9/2018 | |
| WO | WO-2018/170201 A1 | 9/2018 | |
| WO | WO-2018/170203 A1 | 9/2018 | |
| WO | WO-2018/170204 A1 | 9/2018 | |
| WO | WO-2018170203 A1 * | 9/2018 | ........... C07D 495/14 |
| WO | WO-2020/236636 A1 | 11/2020 | |

(Continued)

OTHER PUBLICATIONS

Anderson, D.R. et al., Benzothiophene inhibitors of MK2. Part 1: Structure-activity relationships assessments of selectivity and cellular potency, Bioorganic & Medicinal Chemistry Letters, 19: 4878-4881 (2009).

Anderson, D.R. et al., Benzothiophene inhibitors of MK2. Part 2: Improvements in kinase selectivity and cell potency, Bioorganic & Medicinal Chemistry Letters, 19: 4882-4884 (2009).

Dimsdale, M. J., The Formation of 2-Alkoxyquinolines from Quinoline N-Oxides in Alcoholic Media, J. Heterocyclic Chem., 16:1209-1211 (1979).

International Search Report for PCT/US2015/050495, 2 pages (Dec. 11, 2015).

Lian, Y. et al., Preparation of Heteroaryl Ethers from Azine N-Oxides and Alcohols, Org. Lett., 18:1362-1365 (2016).

(Continued)

*Primary Examiner* — John S Kenyon

(74) *Attorney, Agent, or Firm* — Mintz Levin Cohn Ferris Glovsky and Popeo, P.C.

(57) ABSTRACT

The present disclosure provides novel synthetic intermediates useful in the synthesis of MK2 kinase inhibitors.

20 Claims, No Drawings

(56) References Cited

FOREIGN PATENT DOCUMENTS

WO     WO-2022/020562 A1     1/2022
WO     WO-2022/165148 A1     8/2022

OTHER PUBLICATIONS

Natesan, S. et al., Binding Affinity Prediction for Ligans and Receptors Forming Tautomers and Ionization Species: Inhibition of Mitogen-Activated Protein Kinase-Activated Protein Kinase 2 (MK2), Journal of Medicinal Chemistry, 55(5): 2035-2047 (2012).
International Search Report for PCT/US22/14272, 3 pages (Jun. 21, 2022).
Therrein, E. et al., 1,2-Diamines as inhibitors of co-activator associated arginine methyltransferase 1 (CARM1), Bioorganic and Medicinal Chemistry Letteres, 19(23): 6725-6732 (2009).

* cited by examiner

MK2 INHIBITORS, THE SYNTHESIS THEREOF, AND INTERMEDIATES THERETO

CROSS REFERENCE TO RELATED APPLICATIONS

This application claims the benefit of U.S. Provisional Application No. 63/144,361, filed Feb. 1, 2021, which is herein incorporated by reference in its entirety.

TECHNICAL FIELD OF THE INVENTION

The present disclosure relates to the synthesis of compounds useful as inhibitors of MK2 kinases. The disclosure also provides novel synthetic intermediates useful in the synthesis of MK2 kinase inhibitors.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNF-α), interleukin 6 (IL-6) and interferon gamma (IFNγ), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α. (see Deak et al., *EMBO*. 17:4426-4441 (1998); Shi et al., *Biol. Chem*. 383:1519-1536 (2002); Staklatvala., *Curr. Opin. Pharmacol*. 4:372-377 (2004), and Shiroto et al., *J. Mol. Cardiol*. 38:93-97 (2005)).

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

As described herein, in some embodiments, the present invention provides methods for preparing compounds useful as inhibitors of protein kinases. Such compounds include compound I:

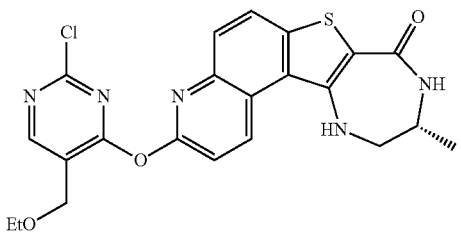

or a pharmaceutically acceptable salt thereof.

In particular, in some embodiments, the present disclosure provides methods of preparing a compound of formula I-a:

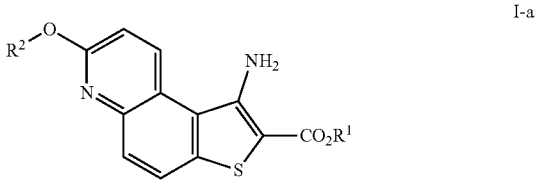

or a salt thereof, wherein each of $R^1$ and $R^2$ is as defined below and described herein.

Additionally or alternatively, in some embodiments, the present disclosure provides methods of preparing a compound of formula I-b:

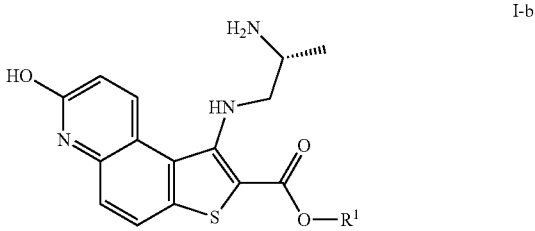

or a salt thereof, wherein:
$R^1$ is defined below and described herein.

Additionally or alternatively, in some embodiments, the present disclosure provides methods of preparing a compound of formula I-c:

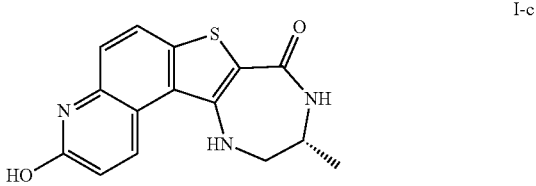 [SMILES: C[C@@H]1CNc2c(sc3ccc4nc(O)ccc4c23)C(=O)N1]

or a salt thereof

In some embodiments, the present disclosure also provides novel intermediates useful in the synthesis of a compound of formula I-a, I-b, or I-c.

BRIEF DESCRIPTION OF CERTAIN EMBODIMENTS OF THE INVENTION

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Examplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), $^+$NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "inhibitor" is defined as a compound that binds to and/or inhibits a kinase with measurable affinity. In certain embodiments, an inhibitor has an $IC_{50}$ and/or binding constant of less about 50 μM, less than about 1 μM, less than about 500 nM, less than about 100 nM, less than about 10 nM, or less than about 1 nM.

As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

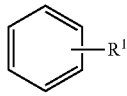

refers to at least

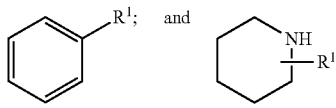

refers to at least

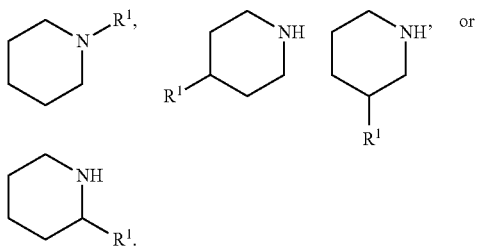

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of sub stituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^°$; —(CH$_2$)$_{0-4}$OR$^°$; —O(CH$_2$)$_{0-4}$R$^°$, —O—(CH$_2$)$_{0-4}$C(O)OR$^°$; —(CH$_2$)$_{0-4}$CH(OR$^°$)$_2$; —(CH$_2$)$_{0-4}$SR$^°$; —(CH$_2$)$_{0-4}$Ph, which may be substituted with R$^°$; —(CH$_2$)$_{0-4}$O(CH$_2$)$_{0-1}$Ph which may be substituted with R$^°$; —CH=CHPh, which may be substituted with R$^°$; —(CH$_2$)$_{0-4}$O(CH$_2$)$_{0-1}$-pyridyl which may be substituted with R$^°$; —NO$_2$; —CN; —N$_3$; —(CH$_2$)$_{0-4}$N(R$^°$)$_2$; —(CH$_2$)$_{0-4}$N(R$^°$)C(O)R$^°$; —N(R$^°$)C(S)R$^°$; —(CH$_2$)$_{0-4}$N(R$^°$)C(O)NR$^°$$_2$; —N(R$^°$)C(S)NR$^°$$_2$, —(CH$_2$)$_{0-4}$N(R$^°$)C(O)OR$^°$; —N(R$^°$)N(R$^°$)C(O)R$^°$; —N(R$^°$)N(R$^°$)C(O)NR$^°$$_2$; —N(R$^°$)N(R$^°$)C(O)OR$^°$; —(CH$_2$)$_{0-4}$C(O)R$^°$; —C(S)R$^°$; —(CH$_2$)$_{0-4}$C(O)OR$^°$; —CH$_2$)$_{0-4}$C(O)SR$^°$; —(CH$_2$)$_{0-4}$C(O)OSiR$^°$$_3$; —(CH$_2$)$_{0-4}$OC(O)R$^°$; —OC(O)(CH$_2$)$_{0-4}$SR—, SC(S)SR$^°$; —(CH$_2$)$_{0-4}$SC(O)R$^°$; —(CH$_2$)$_{0-4}$C(O)NR$^°$$_2$; —C(S)NR$^°$$_2$; —C(S)SR$^°$; —SC(S)SR$^°$, —(CH$_2$)$_{0-4}$OC(O)NR$^°$$_2$; —C(O)N(OR$^°$)R$^°$; —C(O)C(O)R$^°$; —C(O)CH$_2$C(O)R$^°$; —C(NOR$^°$)R$^°$; —(CH$_2$)$_{0-4}$SSR$^°$; —(CH$_2$)$_{0-4}$S(O)$_2$R$^°$; —(CH$_2$)$_{0-4}$S(O)$_2$OR$^°$; —(CH$_2$)$_{0-4}$OS(O)$_2$R$^°$; —S(O)$_2$NR$^°$$_2$; —(CH$_2$)$_{0-4}$S(O)R$^°$; —N(R$^°$)S(O)$_2$NR$^°$$_2$; —N(R$^°$)S(O)$_2$R$^°$; —N(OR$^°$)R$^°$; —C(NH)NR$^°$$_2$; —P(O)$_2$R$^°$; —P(O)R$^°$$_2$; —OP(O)R$^°$$_2$; —OP(O)(OR$^°$)$_2$; SiR$^°$$_3$; —(C$_{1-4}$ straight or branched alkylene)O—N(R$^°$)$_2$; or —(C$_{1-4}$ straight or branched)alkylene)C(O)O—N(R$^°$)$_2$, wherein each R$^°$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^°$ (or the ring formed by taking two independent occurrences of R$^°$ together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●$$_2$, —NO$_2$, —SiR$^●$$_3$, —OSiR$^●$$_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^°$ include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●$$_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$NR$^†$$_2$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\dagger$, -(halo$R^\dagger$), —OH, —$OR^\dagger$, —O(halo$R^\dagger$), —CN, —C(O)OH, —C(O)$OR^\dagger$, —$NH_2$, —$NHR^\dagger$, —$NR^\dagger_2$, or —$NO_2$, wherein each $R^\dagger$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Compounds

As described herein, in some embodiments, the present invention provides methods for preparing compounds useful as inhibitors of protein kinases. Such compounds include compound I:

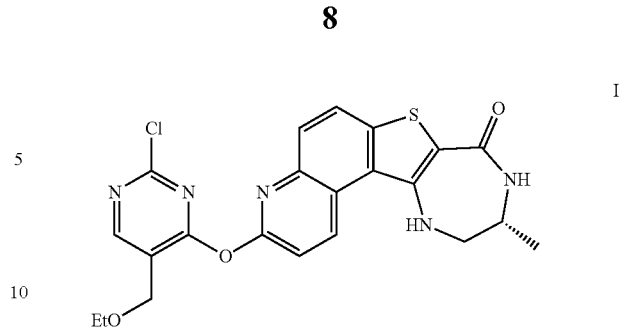

or a pharmaceutically acceptable salt thereof.

The synthesis of Compound I is described in Example 82 of WO 2016/044463, published on Mar. 24, 2016 ("the '463 application"). This synthesis, depicted in Scheme 1 below, consists of 12 chemical transformation steps with a combined yield of about 1.8% for the longest linear sequence.

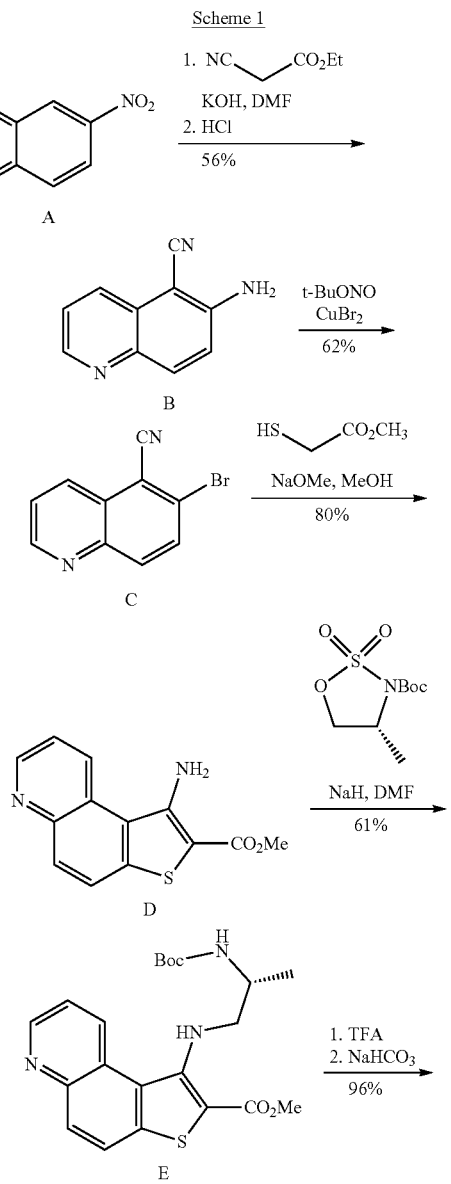

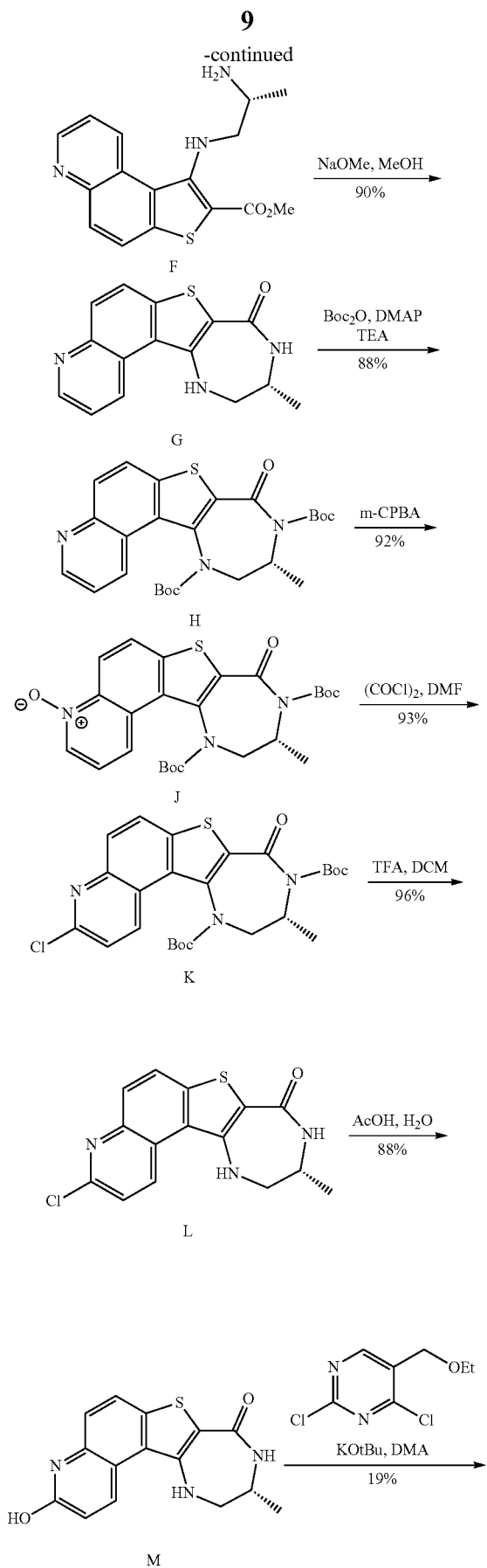

It is understood that yields may vary between different batches, and any referenced or reported yields herein are understood to be exemplary.

The synthesis of Compound I is also described in WO 2018/170203, published Sep. 20, 2018 ("the '203 publication"). The '203 publication describes certain improvements to the synthesis described in the '463 publication, namely a streamlined synthesis of intermediate M in Scheme 1 by, inter alia, moving the five-step oxidation/rearrangement sequence depicted in the transformation of G to M in Scheme 1 to an earlier stage of the synthesis. Such synthesis results in a nine-step longest linear sequence for the synthesis of Compound I in 18.5% yield, a more than 10-fold improvement in yield over the synthesis disclosed in the '463 application:

Scheme 2

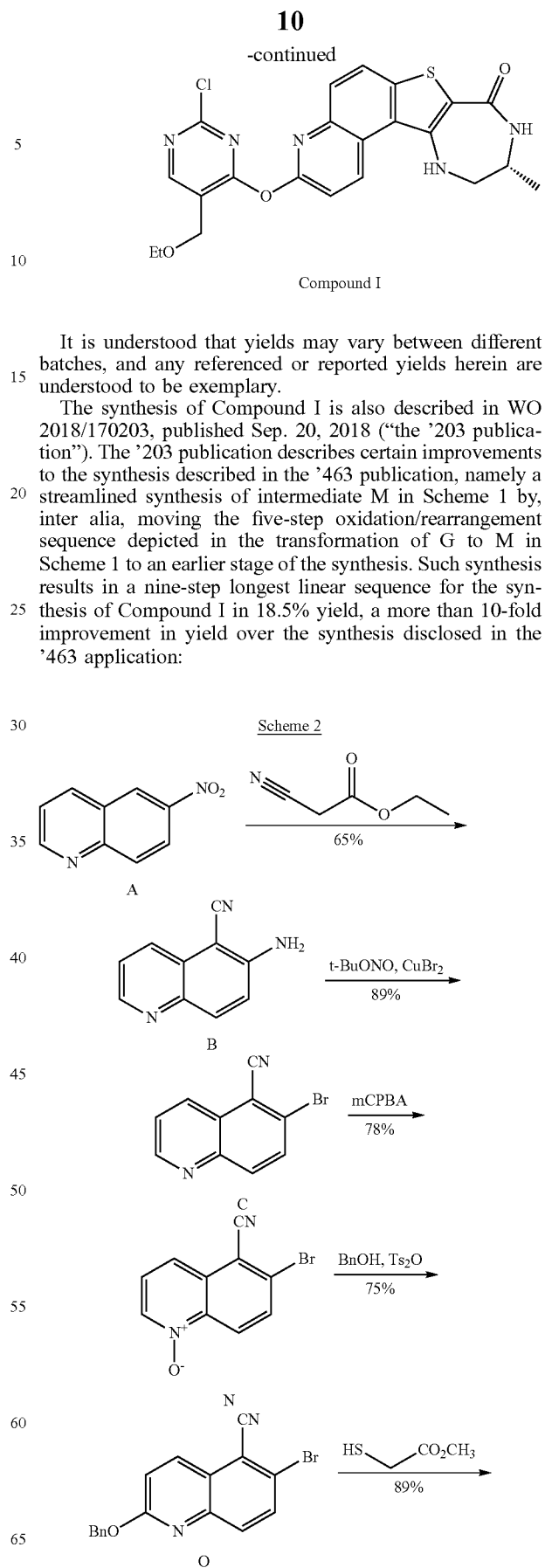

-continued

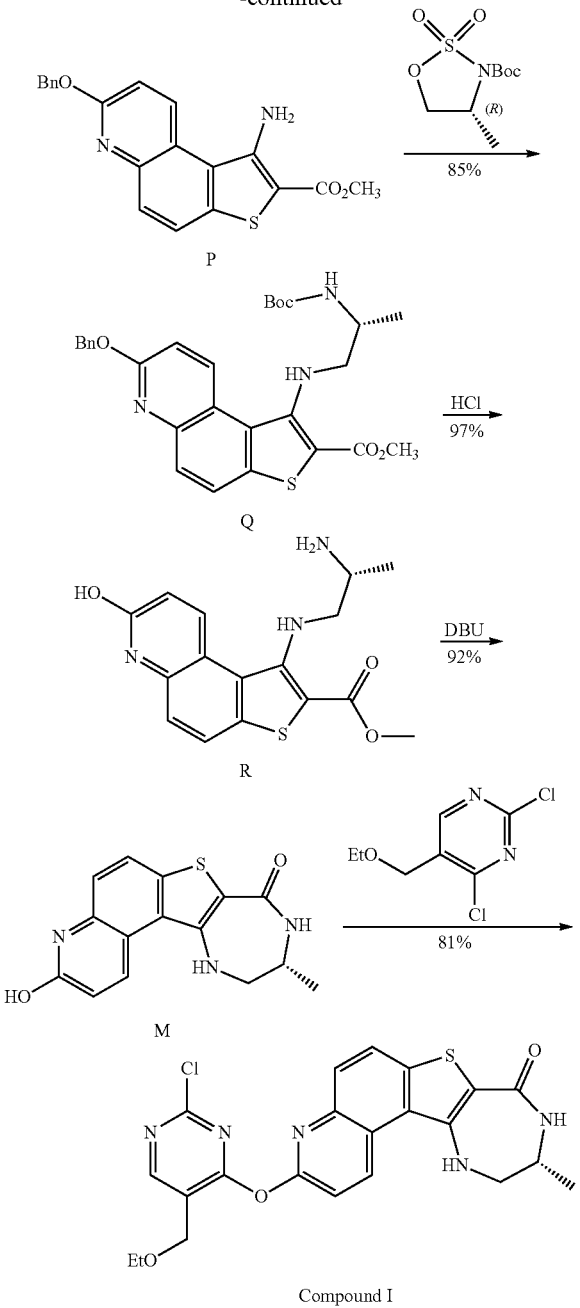

Compound I

While the synthesis of Compound I described in the '203 publication is a marked improvement over the synthesis described in the '463 publication, the synthesis of compound P in Scheme 2 still proceeds via 5 linear steps in 30.12% overall yield. The combined overall yield for the remaining 4 steps in the synthesis of Compound I depicted in Scheme 2 is 61.44%. Thus, the synthesis of compound P in Scheme 2 has a dramatic effect on the combined overall yield of the synthesis of Compound I. Thus, in some embodiments, the present disclosure provides the recognition that even relatively small improvements in the synthetic yield of compound P in Scheme 2 can have a material effect on the yield of the synthesis of Compound I. For example, even a 7% improvement in the yield of the synthesis of compound P in Scheme 2 can result in a 20% increase in the synthesis of Compound I. In some embodiments, the present disclosure provides an improved synthesis of compound P in Scheme 2 (i.e., compound I-a) in a yield of at least 37%, thereby resulting in an overall yield in the synthesis of Compound I of at least 22.7%.

Additionally, it will be appreciated that the synthesis of Compound I described in the '463 publication includes several steps that utilize oxidizing or caustic agents and/or proceed through highly unstable intermediates (e.g., a diazonium salt). Accordingly, in some embodiments, the present disclosure provides the recognition that the synthesis of, e.g., compound P in Scheme 2 can be improved by eliminating the generation of unstable intermediates and/or the use of caustic and/or oxidizing reagents.

Additionally or alternatively, it will be appreciated that the physical and/or chemical properties of certain intermediate compounds contribute to the overall yield of the synthesis of Compound I and/or help control impurities, particularly when scaling-up the synthesis. Accordingly, in some embodiments, the present disclosure provides the recognition that the synthesis of, e.g., compounds R and M in Scheme 2, can be improved by generating one or more particular form(s) with improved physical and/or chemical properties. In some embodiments, an improved form is a salt. In some embodiments, an improved form is a solvate. In some embodiments, an improved form is unsolvated.

In some embodiments, the present disclosure provides an improved synthesis of a compound of formula I-a:

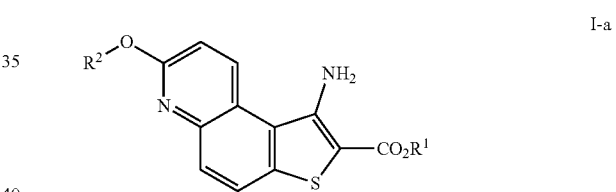

or a salt thereof, wherein each of $R^1$ and $R^2$ is as defined below and described herein.

In some embodiments, compound I-a, or a salt thereof, is prepared according to Scheme 3:

Scheme 3

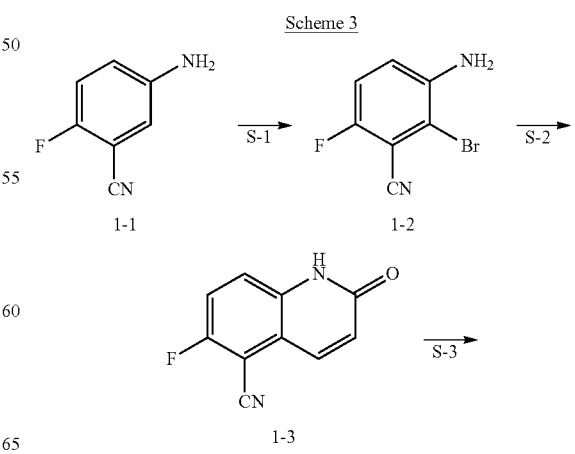

-continued

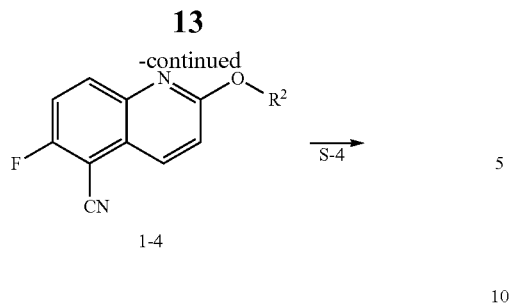

1-4

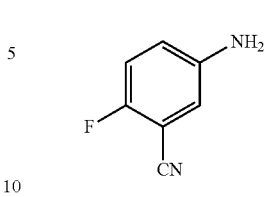

I-a wherein each of R¹ and R² is as defined above and described herein.

It will be appreciated that compounds described herein, e.g., compounds in Scheme 3 or 4, may be in salt form. For example, compounds in Scheme 3 or 4 which contain a basic nitrogen atom may form a salt with a suitable acid. Thus, an NH₂ group may be represented as NH₃⁺ and may associate with a suitable negatively charged counterion. Alternatively and/or additionally, it will be appreciated that certain —OH groups, such as when R² is hydrogen in compound 1-4 or compound I-a in Scheme 3 or in a compound of formulae I-b or I-c, may form a salt with a suitable base. For example, an OH group may be represented as O⁻ and associate with a suitable positively charged counterion. Suitable counterions are well known in the art, e.g., see generally, *March's Advanced Organic Chemistry: Reactions, Mechanisms, and Structure*, M. B. Smith and J. March, 5ᵗʰ Edition, John Wiley & Sons, 2001. All forms and types of salts are contemplated by and are within the scope of the invention.

Step S-1 of Scheme 3

At step S-1, commercially available compound 1-1 is brominated to afford a compound of formula 1-2, or a salt thereof:

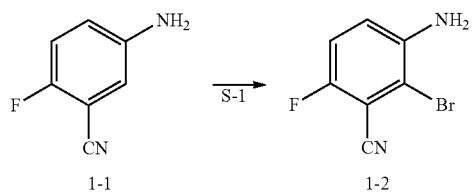

In some embodiments, at step S-1, a compound of formula 1-2, or a salt thereof, is prepared by a method comprising the step of contacting the compound of formula 1-1, or a salt thereof, with a brominating agent. Accordingly, in some embodiments, at step S-1, a compound of formula 1-2, or a salt thereof, is prepared by a method comprising:

(a) providing a compound of formula 1-1:

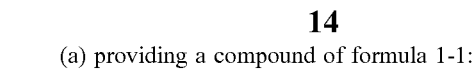

1-1 or a salt thereof; and (b) contacting the compound of formula 1-1, or a salt thereof, with a brominating agent under conditions suitable to afford a compound of formula 1-2, or a salt thereof.

In some embodiments of step S-1, the brominating agent is N-bromosuccinimide.

In some embodiments of step S-1, the brominating agent is sodium bromate/hydrobromic acid (NaBrO₃/HBr).

In some embodiments of step S-1, the brominating agent is selected from phosphorous tribromide (PBr₃), bromine(I) chloride (BrCl), aluminum(III) bromide (e.g., AlBr₃, Al₂Br₆, or AlBr₃·H₂O), and iron(III) bromide and bromine (FeBr₃/Br₂).

Step S-2 of Scheme 3

At step S-2, a compound of formula 1-2, or a salt thereof, is coupled to an acrylate ester of formula 1-2-a to afford a compound of formula 1-3, or a salt thereof:

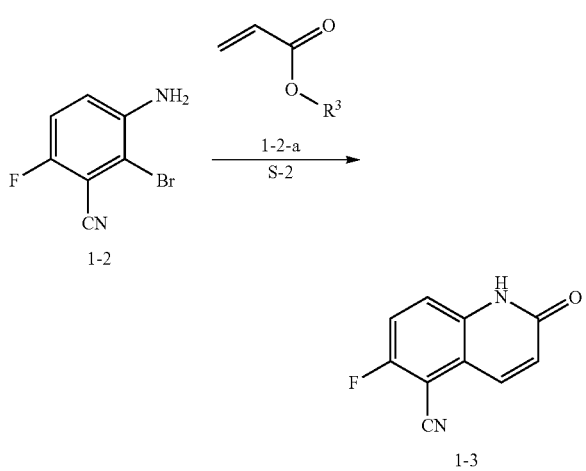

In some embodiments, at step S-2, a compound of formula 1-3, or a salt thereof, is prepared by a method comprising the step of contacting the compound of formula 1-2, or a salt thereof, with an acrylate ester of formula 1-2-a. Accordingly, in some embodiments, at step S-2, a compound of formula 1-3, or a salt thereof, is prepared by a method comprising:

(a) providing a compound of formula 1-2:

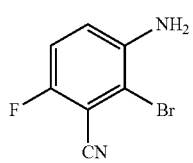

1-2 or a salt thereof; and (b) contacting the compound of formula 1-2, or a salt thereof, with an acrylate ester of formula 1-2-a:

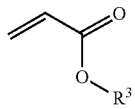

1-2-a wherein:

R³ is optionally substituted $C_{1-6}$ aliphatic;

under conditions suitable to afford a compound of formula 1-3, or a salt thereof.

In some embodiments of step S-2, the conditions suitable to afford a compound of formula 1-3, or a salt thereof, comprise a transition metal catalyst. In some such embodiments, the transition metal catalyst is a palladium catalyst. In some embodiments, the palladium catalyst is a palladium(II) catalyst such as palladium(II) acetate ($Pd(OAc)_2$) or palladium(II) chloride ($PdCl_2$). In some embodiments, the conditions suitable to afford a compound of formula 1-3, or a salt thereof, further comprise a phosphine ligand. In some embodiments, compound 1-2, or a salt thereof, is coupled to an acrylate ester of formula 1-2-a in the presence of a palladium catalyst and, optionally, a phosphine ligand. In some embodiments, a phosphine ligand is selected from the group consisting of $PPh_3$, $P(o-Tol)_3$, $PPh_2Cy$, $PPhCy_2$, $P^tBu_2Me$, $PCy_3$, $PCy_3$—$BF_4$, APhos, JohnPhos, CyJohnPhos, DavePhos, XPhos, $^tBu$-XPhos, SPhos, $P(fur)_3$, RuPhos, $^{me}CgPPh$, DCPE, DPPP, DPPF, DCyPF, DPEphos, DCEPhos, Xantphos, Cy-Xantphos, $P^tBu_2Me$-$HBF_4$, $P^tBu_3$-$HBF_4$, and cataCXium A.

In some embodiments, the palladium catalyst is a palladium(0) catalyst such as tetrakis(triphenylphosphine)palladium(0). In some embodiments of step S-2, the compound of formula 1-3, or a salt thereof, is prepared under Heck reaction conditions.

In some embodiments, conditions suitable to afford a compound of formula 1-3, or a salt thereof, are selected from

| No. | Palladium catalyst | Ligand |
|---|---|---|
| 1 | $Pd(OAc)_2$ | $PPh_3$ (CAS 603-35-0) |
| 2 | $Pd(OAc)_2$ | $P(o-Tol)_3$ (CAS 6163-58-2) |
| 3 | $Pd(OAc)_2$ | $PPh_2Cy$ (CAS 6372-42-5) |
| 4 | $Pd(OAc)_2$ | $PPhCy_2$ (CAS 6476-37-5) |
| 5 | $Pd(OAc)_2$ | $P^tBu_2Me$ (CAS 6002-40-0) |
| 6 | $Pd(OAc)_2$ | $PCy_3$ (CAS 2622-14-2) |
| 7 | $Pd(OAc)_2$ | $PCy_3$-$BF_4$ (CAS 58656-04-5) |
| 8 | $Pd(OAc)_2$ | APhos (CAS 932710-63-9) |
| 9 | $Pd(OAc)_2$ | JohnPhos (CAS 224311-51-7) |
| 10 | $Pd(OAc)_2$ | CyJohnPhos (CAS 247940-06-3) |
| 11 | $Pd(OAc)_2$ | DavePhos (CAS 213697-53-1) |
| 12 | $Pd(OAc)_2$ | XPhos (CAS 564483-18-7) |
| 13 | $Pd(OAc)_2$ | $^tBu$—XPhos (CAS 564483-19-8) |
| 14 | $Pd(OAc)_2$ | SPhos (CAS 657408-07-6) |
| 15 | $Pd(OAc)_2$ | $P(fur)_3$ (CAS 5518-52-5) |
| 16 | $Pd(OAc)_2$ | RuPhos (CAS 787618-22-8) |
| 17 | $Pd(OAc)_2$ | $^{me}CgPPh$ (CAS 97739-46-3) |
| 18 | $Pd(OAc)_2$ | DCPE (CAS 23743-26-2) |
| 19 | $Pd(OAc)_2$ | DPPP (CAS 6737-42-4) |
| 20 | $Pd(OAc)_2$ | DPPF (CAS 12150-46-8) |
| 21 | $Pd(OAc)_2$ | DCyPF (CAS 146960-90-9) |
| 22 | $Pd(OAc)_2$ | DPEphos (CAS 166330-10-5) |
| 23 | $Pd(OAc)_2$ | DCEPhos (CAS 434336-16-0) |
| 24 | $Pd(OAc)_2$ | Xantphos (CAS 161265-03-8) |
| 25 | $Pd(OAc)_2$ | Cy-Xantphos (CAS 940934-47-4) |
| 26 | $Pd(OAc)_2$ | $P^tBu_2Me$-$HBF_4$ (CAS 479094-62-7) |
| 27 | $Pd(OAc)_2$ | $P^tBu_3$-$HBF_4$ (CAS 131274-22-1) |
| 28 | $Pd(OAc)_2$ | cataCXium A (CAS 321921-71-5) |
| 29 | $Pd(PPh_3)_2Cl_2$ (CAS 13965-03-2) | — |
| 30 | $Pd(amphos)Cl_2$ (CAS 887919-35-9) | — |
| 31 | SPhos-Pd-G1, MTBE adduct (CAS 1028206-58-7) | — |
| 32 | SPhos-Pd-G2 (CAS 1375325-64-6) | — |
| 33 | SPhos-Pd-G3 (CAS 1445085-82-4) | — |
| 34 | SPhos-Pd-G4 (CAS 1599466-87-1) | — |
| 35 | $Pd(xantphas)Cl_2$ (CAS 205319-10-4) | — |
| 36 | $Pd_2(dba)_3$ | $PPh_3$ (CAS 603-35-0) |
| 37 | $Pd_2(dba)_3$ | $P(o-Tol)_3$ (CAS 6163-58-2) |
| 38 | $Pd_2(dba)_3$ | $PPh_2Cy$ (CAS 6372-42-5) |
| 39 | $Pd_2(dba)_3$ | $PPhCy_2$ (CAS 6476-37-5) |
| 40 | $Pd_2(dba)_3$ | $P^tBu_2Me$ (CAS 6002-40-0) |
| 41 | $Pd_2(dba)_3$ | $PCy_3$ (CAS 2622-14-2) |
| 42 | $Pd_2(dba)_3$ | $PCy_3$-$BF_4$ (CAS 58656-04-5) |
| 43 | $Pd_2(dba)_3$ | APhos (CAS 932710-63-9) |
| 44 | $Pd_2(dba)_3$ | JohnPhos (CAS 224311-51-7) |
| 45 | $Pd_2(dba)_3$ | CyJohnPhos (CAS 247940-06-3) |
| 46 | $Pd_2(dba)_3$ | DavePhos (CAS 213697-53-1) |
| 47 | $Pd_2(dba)_3$ | XPhos (CAS 564483-18-7) |
| 48 | $Pd_2(dba)_3$ | $^tBu$-XPhos (CAS 564483-19-8) |
| 49 | $Pd_2(dba)_3$ | SPhos (CAS 657408-07-6) |
| 50 | $Pd_2(dba)_3$ | $P(fur)_3$ (CAS 5518-52-5) |
| 51 | $Pd_2(dba)_3$ | RuPhos (CAS 787618-22-8) |
| 52 | $Pd_2(dba)_3$ | $^{me}CgPPh$ (CAS 97739-46-3) |
| 53 | $Pd_2(dba)_3$ | DCPE (CAS 23743-26-2) |
| 54 | $Pd_2(dba)_3$ | DPPP (CAS 6737-42-4) |
| 55 | $Pd_2(dba)_3$ | DPPF (CAS 12150-46-8) |
| 56 | $Pd_2(dba)_3$ | DCyPF (CAS 146960-90-9) |
| 57 | $Pd_2(dba)_3$ | DPEphos (CAS 166330-10-5) |
| 58 | $Pd_2(dba)_3$ | DCEPhos (CAS 434336-16-0) |
| 59 | $Pd_2(dba)_3$ | Xantphos (CAS 161265-03-8) |
| 60 | $Pd_2(dba)_3$ | Cy-Xantphos (CAS 940934-47-4) |
| 61 | $Pd_2(dba)_3$ | $P^tBu_2Me$-$HBF_4$ (CAS 479094-62-7) |
| 62 | $Pd_2(dba)_3$ | $P^tBu_3$-$HBF_4$ (CAS 131274-22-1) |
| 63 | $Pd_2(dba)_3$ | cataCXium A (CAS 321921-71-5) |
| 64 | $PdCl_2$ CAS 7647-10-1 | $PPh_3$ (CAS 603-35-0) |
| 65 | $PdCl_2$ CAS 7647-10-1 | $P(o-Tol)_3$ (CAS 6163-58-2) |
| 66 | $PdCl_2$ CAS 7647-10-1 | $PPh_2Cy$ (CAS 6372-42-5) |
| 67 | $PdCl_2$ CAS 7647-10-1 | $PPhCy_2$ (CAS 6476-37-5) |
| 68 | $PdCl_2$ CAS 7647-10-1 | $P^tBu_2Me$ (CAS 6002-40-0) |
| 69 | $PdCl_2$ CAS 7647-10-1 | $PCy_3$ (CAS 2622-14-2) |
| 70 | $PdCl_2$ CAS 7647-10-1 | $PCy_3$-$BF_4$ (CAS 58656-04-5) |
| 71 | $PdCl_2$ CAS 7647-10-1 | APhos (CAS 932710-63-9) |
| 72 | $PdCl_2$ CAS 7647-10-1 | JohnPhos (CAS 224311-51-7) |
| 73 | $PdCl_2$ CAS 7647-10-1 | CyJohnPhos (CAS 247940-06-3) |
| 74 | $PdCl_2$ CAS 7647-10-1 | DavePhos (CAS 213697-53-1) |
| 75 | $PdCl_2$ CAS 7647-10-1 | XPhos (CAS 564483-18-7) |
| 76 | $PdCl_2$ CAS 7647-10-1 | $^tBu$-XPhos (CAS 564483-19-8) |
| 77 | $PdCl_2$ CAS 7647-10-1 | SPhos (CAS 657408-07-6) |
| 78 | $PdCl_2$ CAS 7647-10-1 | $P(fur)_3$ (CAS 5518-52-5) |
| 79 | $PdCl_2$ CAS 7647-10-1 | RuPhos (CAS 787618-22-8) |

-continued

| No. | Palladium catalyst | Ligand |
|---|---|---|
| 80 | PdCl$_2$ CAS 7647-10-1 | $^{me}$CgPPh (CAS 97739-46-3) |
| 81 | PdCl$_2$ CAS 7647-10-1 | DCPE (CAS 23743-26-2) |
| 82 | PdCl$_2$ CAS 7647-10-1 | DPPP (CAS 6737-42-4) |
| 83 | PdCl$_2$ CAS 7647-10-1 | DPPF (CAS 12150-46-8) |
| 84 | PdCl$_2$ CAS 7647-10-1 | DCyPF (CAS 146960-90-9) |
| 85 | PdCl$_2$ CAS 7647-10-1 | DPEphos (CAS 166330-10-5) |
| 86 | PdCl$_2$ CAS 7647-10-1 | DCEPhos (CAS 434336-16-0) |
| 87 | PdCl$_2$ CAS 7647-10-1 | Xantphos (CAS 161265-03-8) |
| 88 | PdCl$_2$ CAS 7647-10-1 | Cy-Xantphos (CAS 940934-47-4) |
| 89 | PdCl$_2$ CAS 7647-10-1 | P$^t$Bu$_2$Me-HBF$_4$ (CAS 479094-62-7) |
| 90 | PdCl$_2$ CAS 7647-10-1 | P$^t$Bu$_3$-HBF$_4$ (CAS 131274-22-1) |
| 91 | PdCl$_2$ CAS 7647-10-1 | cataCXium A (CAS 321921-71-5) |
| 92 | Pd(cod)Cl$_2$ CAS 12107-56-1 | PPh$_3$ (CAS 603-35-0) |
| 93 | Pd(cod)Cl$_2$ CAS 12107-56-1 | P(o-Tol)$_3$ (CAS 6163-58-2) |
| 94 | Pd(cod)Cl$_2$ CAS 12107-56-1 | PPh$_2$Cy (CAS 6372-42-5) |
| 95 | Pd(cod)Cl$_2$ CAS 12107-56-1 | PPhCy$_2$ (CAS 6476-37-5) |
| 96 | Pd(cod)Cl$_2$ CAS 12107-56-1 | P$^t$Bu$_2$Me (CAS 6002-40-0) |
| 97 | Pd(cod)Cl$_2$ CAS 12107-56-1 | PCy$_3$ (CAS 2622-14-2) |
| 98 | Pd(cod)Cl$_2$ CAS 12107-56-1 | PCy$_3$-BF$_4$ (CAS 58656-04-5) |
| 99 | Pd(cod)Cl$_2$ CAS 12107-56-1 | APhos (CAS 932710-63-9) |
| 100 | Pd(cod)Cl$_2$ CAS 12107-56-1 | JohnPhos (CAS 224311-51-7) |
| 101 | Pd(cod)Cl$_2$ CAS 12107-56-1 | CyJohnPhos (CAS 247940-06-3) |
| 102 | Pd(cod)Cl$_2$ CAS 12107-56-1 | DavePhos (CAS 213697-53-1) |
| 103 | Pd(cod)Cl$_2$ CAS 12107-56-1 | XPhos (CAS 564483-18-7) |
| 104 | Pd(cod)Cl$_2$ CAS 12107-56-1 | $^t$Bu-XPhos (CAS 564483-19-8) |
| 105 | Pd(cod)Cl$_2$ CAS 12107-56-1 | SPhos (CAS 657408-07-6) |
| 106 | Pd(cod)Cl$_2$ CAS 12107-56-1 | P(fur)$_3$ (CAS 5518-52-5) |
| 107 | Pd(cod)Cl$_2$ CAS 12107-56-1 | RuPhos (CAS 787618-22-8) |
| 108 | Pd(cod)Cl$_2$ CAS 12107-56-1 | $^{me}$CgPPh (CAS 97739-46-3) |
| 109 | Pd(cod)Cl$_2$ CAS 12107-56-1 | DCPE (CAS 23743-26-2) |
| 110 | Pd(cod)Cl$_2$ CAS 12107-56-1 | DPPP (CAS 6737-42-4) |
| 111 | Pd(cod)Cl$_2$ CAS 12107-56-1 | DPPF (CAS 12150-46-8) |
| 112 | Pd(cod)Cl$_2$ CAS 12107-56-1 | DCyPF (CAS 146960-90-9) |
| 113 | Pd(cod)Cl$_2$ CAS 12107-56-1 | DPEphos (CAS 166330-10-5) |
| 114 | Pd(cod)Cl$_2$ CAS 12107-56-1 | DCEPhos (CAS 434336-16-0) |
| 115 | Pd(cod)Cl$_2$ CAS 12107-56-1 | Xantphos (CAS 161265-03-8) |
| 116 | Pd(cod)Cl$_2$ CAS 12107-56-1 | Cy-Xantphos (CAS 940934-47-4) |
| 117 | Pd(cod)Cl$_2$ CAS 12107-56-1 | P$^t$Bu$_2$Me-HBF$_4$ (CAS 479094-62-7) |
| 118 | Pd(cod)Cl$_2$ CAS 12107-56-1 | P$^t$Bu$_3$-HBF$_4$ (CAS 131274-22-1) |
| 119 | Pd(cod)Cl$_2$ CAS 12107-56-1 | cataCXium A (CAS 321921-71-5) |
| 120 | [Pd(allyl)Cl]$_2$ CAS 12012-95-2 | PPh$_3$ (CAS 603-35-0) |
| 121 | [Pd(allyl)Cl]$_2$ CAS 12012-95-2 | P(o-Tol)$_3$ (CAS 6163-58-2) |
| 122 | [Pd(allyl)Cl]$_2$ CAS 12012-95-2 | PPh$_2$Cy (CAS 6372-42-5) |
| 123 | [Pd(allyl)Cl]$_2$ CAS 12012-95-2 | PPhCy$_2$ (CAS 6476-37-5) |
| 124 | [Pd(allyl)Cl]$_2$ CAS 12012-95-2 | P$^t$Bu$_2$Me (CAS 6002-40-0) |
| 125 | [Pd(allyl)Cl]$_2$ CAS 12012-95-2 | PCy$_3$ (CAS 2622-14-2) |
| 126 | [Pd(allyl)Cl]$_2$ CAS 12012-95-2 | PCy$_3$-BF$_4$ (CAS 58656-04-5) |
| 127 | [Pd(allyl)Cl]$_2$ CAS 12012-95-2 | APhos (CAS 932710-63-9) |
| 128 | [Pd(allyl)Cl]$_2$ CAS 12012-95-2 | JohnPhos (CAS 224311-51-7) |
| 129 | [Pd(allyl)Cl]$_2$ CAS 12012-95-2 | CyJohnPhos (CAS 247940-06-3) |
| 130 | [Pd(allyl)Cl]$_2$ CAS 12012-95-2 | DavePhos (CAS 213697-53-1) |
| 131 | [Pd(allyl)Cl]$_2$ CAS 12012-95-2 | XPhos (CAS 564483-18-7) |
| 132 | [Pd(allyl)Cl]$_2$ CAS 12012-95-2 | $^t$Bu-XPhos (CAS 564483-19-8) |
| 133 | [Pd(allyl)Cl]$_2$ CAS 12012-95-2 | SPhos (CAS 657408-07-6) |
| 134 | [Pd(allyl)Cl]$_2$ CAS 12012-95-2 | P(fur)$_3$ (CAS 5518-52-5) |
| 135 | [Pd(allyl)Cl]$_2$ CAS 12012-95-2 | RuPhos (CAS 787618-22-8) |
| 136 | [Pd(allyl)Cl]$_2$ CAS 12012-95-2 | $^{me}$CgPPh (CAS 97739-46-3) |
| 137 | [Pd(allyl)Cl]$_2$ CAS 12012-95-2 | DCPE (CAS 23743-26-2) |
| 138 | [Pd(allyl)Cl]$_2$ CAS 12012-95-2 | DPPP (CAS 6737-42-4) |
| 139 | [Pd(allyl)Cl]$_2$ CAS 12012-95-2 | DPPF (CAS 12150-46-8) |
| 140 | [Pd(allyl)Cl]$_2$ CAS 12012-95-2 | DCyPF (CAS 146960-90-9) |
| 141 | [Pd(allyl)Cl]$_2$ CAS 12012-95-2 | DPEphos (CAS 166330-10-5) |
| 142 | [Pd(allyl)Cl]$_2$ CAS 12012-95-2 | DCEPhos (CAS 434336-16-0) |
| 143 | [Pd(allyl)Cl]$_2$ CAS 12012-95-2 | Xantphos (CAS 161265-03-8) |
| 144 | [Pd(allyl)Cl]$_2$ CAS 12012-95-2 | Cy-Xantphos (CAS 940934-47-4) |
| 145 | [Pd(allyl)Cl]$_2$ CAS 12012-95-2 | P$^t$Bu$_2$Me-HBF$_4$ (CAS 479094-62-7) |
| 146 | [Pd(allyl)Cl]$_2$ CAS 12012-95-2 | PtBu$_3$-HBF$_4$ (CAS 131274-22-1) |
| 147 | [Pd(allyl)Cl]$_2$ CAS 12012-95-2 | cataCXium A (CAS 321921-71-5) |
| 148 | [Pd(cinnamyl)Cl]$_2$ CAS 12131-44-1 | PPh$_3$ (CAS 603-35-0) |
| 149 | [Pd(cinnamyl)Cl]$_2$ CAS 12131-44-1 | P(o-Tol)$_3$ (CAS 6163-58-2) |
| 150 | [Pd(cinnamyl)Cl]$_2$ CAS 12131-44-1 | PPh$_2$Cy (CAS 6372-42-5) |
| 151 | [Pd(cinnamyl)Cl]$_2$ CAS 12131-44-1 | PPhCy$_2$ (CAS 6476-37-5) |
| 152 | [Pd(cinnamyl)Cl]$_2$ CAS 12131-44-1 | P$^t$Bu$_2$Me (CAS 6002-40-0) |
| 153 | [Pd(cinnamyl)Cl]$_2$ CAS 12131-44-1 | PCy$_3$ (CAS 2622-14-2) |

-continued

| No. | Palladium catalyst | Ligand |
|---|---|---|
| 154 | [Pd(cinnamyl)Cl]$_2$ CAS 12131-44-1 | PCy$_3$-BF$_4$ (CAS 58656-04-5) |
| 155 | [Pd(cinnamyl)Cl]$_2$ CAS 12131-44-1 | APhos (CAS 932710-63-9) |
| 156 | [Pd(cinnamyl)Cl]$_2$ CAS 12131-44-1 | JohnPhos (CAS 224311-51-7) |
| 157 | [Pd(cinnamyl)Cl]$_2$ CAS 12131-44-1 | CyJohnPhos (CAS 247940-06-3) |
| 158 | [Pd(cinnamyl)Cl]$_2$ CAS 12131-44-1 | DavePhos (CAS 213697-53-1) |
| 159 | [Pd(cinnamyl)Cl]$_2$ CAS 12131-44-1 | XPhos (CAS 564483-18-7) |
| 160 | [Pd(cinnamyl)Cl]$_2$ CAS 12131-44-1 | $^t$Bu-XPhos (CAS 564483-19-8) |
| 161 | [Pd(cinnamyl)Cl]$_2$ CAS 12131-44-1 | SPhos (CAS 657408-07-6) |
| 162 | [Pd(cinnamyl)Cl]$_2$ CAS 12131-44-1 | P(fur)$_3$ (CAS 5518-52-5) |
| 163 | [Pd(cinnamyl)Cl]$_2$ CAS 12131-44-1 | RuPhos (CAS 787618-22-8) |
| 164 | [Pd(cinnamyl)Cl]$_2$ CAS 12131-44-1 | $^{me}$CgPPh (CAS 97739-46-3) |
| 165 | [Pd(cinnamyl)Cl]$_2$ CAS 12131-44-1 | DCPE (CAS 23743-26-2) |
| 166 | [Pd(cinnamyl)Cl]$_2$ CAS 12131-44-1 | DPPP (CAS 6737-42-4) |
| 167 | [Pd(cinnamyl)Cl]$_2$ CAS 12131-44-1 | DPPF (CAS 12150-46-8) |
| 168 | [Pd(cinnamyl)Cl]$_2$ CAS 12131-44-1 | DCyPF (CAS 146960-90-9) |
| 169 | [Pd(cinnamyl)Cl]$_2$ CAS 12131-44-1 | DPEphos (CAS 166330-10-5) |
| 170 | [Pd(cinnamyl)Cl]$_2$ CAS 12131-44-1 | DCEPhos (CAS 434336-16-0) |
| 171 | [Pd(cinnamyl)Cl]$_2$ CAS 12131-44-1 | Xantphos (CAS 161265-03-8) |
| 172 | [Pd(cinnamyl)Cl]$_2$ CAS 12131-44-1 | Cy-Xantphos (CAS 940934-47-4) |
| 173 | [Pd(cinnamyl)Cl]$_2$ CAS 12131-44-1 | P$^t$Bu$_2$Me-HBF$_4$ (CAS 479094-62-7) |
| 174 | [Pd(cinnamyl)Cl]$_2$ CAS 12131-44-1 | P$^t$Bu$_3$-HBF$_4$ (CAS 131274-22-1) |
| 175 | [Pd(cinnamyl)Cl]$_2$ CAS 12131-44-1 | cataCXium A (CAS 321921-71-5) |

In some embodiments, $R^3$ is optionally substituted $C_{1-4}$ aliphatic. In some embodiments, $R^3$ is optionally substituted $C_{1-2}$ aliphatic. In some embodiments, $R^3$ is selected from methyl, ethyl, n-propyl, isopropyl, n-butyl, sec-butyl, isobutyl, and tent-butyl. In some embodiments, $R^3$ is n-butyl.

In some embodiments, e.g., when a lower charge of a palladium catalyst is used at step S-2, a mixture of a compound of formula 1-3 and a compound of formula 1-2-b is produced. In some embodiments, a second catalyst is added to convert a compound of formula 1-2-b to a compound of formula 1-3. In some embodiments, the second catalyst is an acid (e.g., HCl or acetic acid). In some embodiments, the second catalyst is a tertiary amine (e.g., DABCO, DMAP, or DBU). In some embodiments, the second catalyst is a tertiary phospine. In some embodiments, the second metal catalyst is a transition metal catalyst (e.g., is a palladium catalyst). In some embodiments, the palladium catalyst is selected from those described above and herein as suitable for performing the cyclization at step S-2.

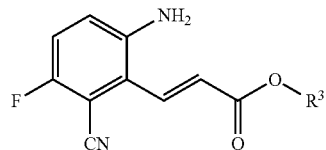

1-2-b

Step S-3 of Scheme 3

At step S-3, a compound of formula 1-3, or a salt thereof, is reacted with an alkyl halide 1-3-a to afford a compound of formula 1-4, or a salt thereof:

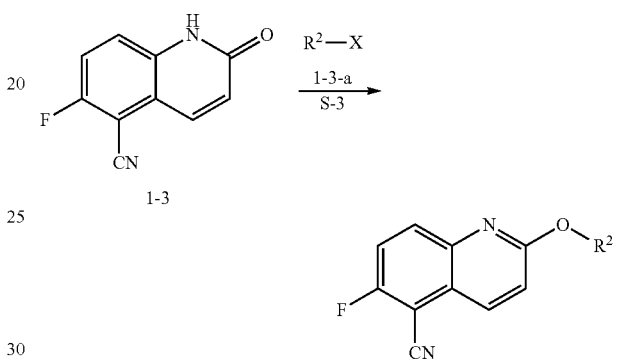

In some embodiments, at step S-3, a compound of formula 1-4, or a salt thereof, is prepared by a method comprising the step of contacting a compound of formula 1-3, or a salt thereof, with an alkyl halide of formula 1-3-a. Accordingly, in some embodiments, at step S-3, a compound of formula 1-4, or a salt thereof, is prepared by a method comprising:
(a) providing a compound of formula 1-3:

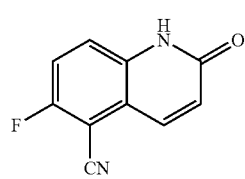

1-3 or a salt thereof; and
(b) contacting the compound of formula 1-3 with a compound of formula 1-3-a:

$$R^2-X \qquad \text{1-3-a}$$

wherein $R^2$ is optionally substituted $C_{1-6}$ aliphatic or —SO$_2$R$^{2a}$,
$R^{2a}$ is an optionally substituted $C_{1-6}$ aliphatic or aryl; and
X is a suitable leaving group;
under conditions suitable to form a compound of formula 1-4, or a salt thereof.

In some embodiments, the conditions suitable to afford a compound of formula 1-4, or a salt thereof, comprise a transition metal catalyst. In some such embodiments, the transition metal catalyst is a palladium catalyst. In some embodiments, the palladium catalyst is a palladium(II) catalyst such as palladium(II) acetate (Pd(OAc)$_2$), palladium(II) chloride (PdCl$_2$), bis(di-tert-butyl(4-dimethylaminophenyl)phosphine)dichloropalladium(II) (Pd(amphos)Cl$_2$).

In some embodiments, the conditions suitable to form a compound of formula 1-4, or a salt thereof, comprises a palladium(II) catalyst without a ligand.

In some embodiments, the conditions suitable to afford a compound of formula 1-4, or a salt thereof, further comprise a ligand. In some such embodiments, the ligand is a phosphine ligand. In some embodiments, a phosphine ligand is SPhos (2-dicyclohexylphosphino-2',6'-dimethoxybiphenyl) or 1,3,5,7-tetramethyl-6-phenyl-2,4,8-trioxa-6-phosphaadamantane ($^{me}$CgPPh).

In some embodiments, compound 1-3, or a salt thereof, is coupled to an alkyl halide of formula 1-3-a in the presence of a palladium catalyst and, optionally, a phosphine ligand.

In some embodiments, the palladium catalyst is a palladium(0) catalyst such as tetrakis(triphenylphosphine)palladium(0) or tris(dibenzylideneacetone)dipalladium(0) (Pd$_2$(dba)$_3$).

In some embodiments, the conditions suitable to afford a compound of formula 1-4, or a salt thereof, are selected from:

| No. | Palladium catalyst | Ligand |
|---|---|---|
| 1 | Pd(OAc)$_2$ | — |
| 2 | Pd(OAc)$_2$ | SPhos |
| 3 | Pd(OAc)$_2$ | $^{me}$CgPPh |
| 4 | Pd(amphos)Cl$_2$ | — |
| 5 | Pd$_2$(dba)$_3$ | — |
| 6 | Pd$_2$(dba)$_3$ | SPhos |

In some embodiments, the conditions suitable to afford a compound of formula 1-4, or a salt thereof, further comprise a base. In some such embodiments, the base is an inorganic base such as potassium carbonate (K$_2$CO$_3$), sodium carbonate (Na$_2$CO$_3$), or cesium carbonate (CsCO$_3$). In some embodiments, the base is an organic base. In some embodiments, the base is an amine base. In some embodiments, the base is trimethylamine. In some embodiments, the base is diisopropylethylamine (DIEA). In some embodiments, the base is triethylamine. In some embodiments, the base is 1,8-diazabicyclo(5.4.0)undec-7-ane (DBU).

In some embodiments, the conditions suitable to afford a compound of formula 1-4, or a salt thereof, further comprise a trifluoromethane sulfonate salt such as sodium triflate (NaOTf). In some such embodiments, a trifluoromethane sulfonate salt is utilized in a catalytic amount.

As defined herein, a suitable "leaving group" that is "subject to nucleophilic displacement" is a chemical group that is readily displaced by a desired incoming nucleophilic chemical entity. Suitable leaving groups are well known in the art, e.g., see generally, *March's Advanced Organic Chemistry: Reactions, Mechanisms, and Structure*, M. B. Smith and J. March, 5$_{th}$ Edition, John Wiley & Sons, 2001. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, phosphonate, sulfoxide, sulphone, and diazonium moieties. For the above mentioned "optionally substituted" moieties, the moieties may be optionally substituted with C$_{1-4}$ aliphatic, fluoro-substituted C$_{1-4}$ aliphatic, halogen, or nitro. Examples of suitable leaving groups include chloro, iodo, bromo, fluoro, sulfoxide, sulphone, methanesulfonyloxy (mesyloxy), tosyloxy, trifly-loxy, benzenesulfonyloxy, nitro-phenylsulfonyloxy (nosyloxy), and bromophenylsulfonyloxy (brosyloxy).

In some embodiments, X is a suitable leaving group as defined above and herein. In some embodiments, X is halogen. In some embodiments, X is chloro. In some embodiments, X is bromo. In some embodiments, X is iodo. In some embodiments, X is fluoro.

In some embodiments of step S-3, R$^2$ is any suitable phenol or ether protecting group. Such groups are described in "Greene's Protective Groups in Organic Synthesis" Fourth Ed. Wuts, P. G. M. and Greene, T. W., Eds., John Wiley & Sons, New York: 2007, the entirety of which is hereby incorporated by reference. In some embodiments, R$^2$ is optionally substituted C$_{1-4}$ aliphatic. In some embodiments, R$^2$ is optionally substituted C$_{1-2}$ aliphatic. In some embodiments, R$^2$ is selected from methyl, ethyl, isopropyl, tert-butyl, cyclohexyl, cyanomethyl (CH$_2$CN), methoxymethyl (CH$_2$OCH$_3$), methoxyethoxymethyl (MEM), benzyl, p-methoxybenzyl (PMB), benzyloxymethyl (BOM), 2-(trimethylsilyl)ethoxymethyl (SEM), methylthiomethyl (MTM), phenylthiomethyl (PTM), 2-chloroethyl (CH$_2$CH$_2$Cl), 2-bromoethyl (CH$_2$CH$_2$Br), cyclopropylmethyl, 2,4-dimethylbenzyl, o-nitrobenzyl, p-nitrobenzyl, 2,6-dichlorobenzyl, and 3,4-dichlorobenzyl. In some embodiments, R$^2$ is selected from benzyl, p-methoxybenzyl (PMB), 2,4-dimethylbenzyl, o-nitrobenzyl, p-nitrobenzyl, 2,6-dichlorobenzyl, and 3,4-dichlorobenzyl. In some embodiments, R$^2$ is benzyl.

In some embodiments, e.g., when a particular X-R$^2$ group is used, the addition of R$^2$ is not entirely regioselective, and a mixture of a compound of formula 1-4, or a salt thereof, and a compound of formula 1-4-a, or a salt thereof, is produced:

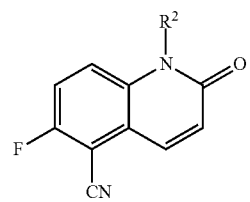

1-4-a

In some embodiments, when conditions suitable to afford a compound of formula 1-4, or a salt thereof, comprise a transition metal catalyst (e.g., palladium catalyst as described above and herein) the amount of a compound of formula 1-4-a, or a salt thereof, generated is reduced or eliminated entirely. However, in some embodiments, even when conditions suitable to afford a compound of formula 1-4, or a salt thereof, comprise a transition metal catalyst (e.g., palladium catalyst as described above and herein), a compound of formula 1-4-a, or a salt thereof, is still produced.

In some embodiments, the present disclosure provides the recognition that use of certain R$^2$ groups (e.g., sulfonyl groups such as —SO$_2$R$^{2a}$) may reduce or eliminate the formation of a compound of formula 1-4-a, or a salt thereof, and may increase yields of a compound of formula 1-4, or a salt thereof. In some embodiments, the present disclosure provides the recognition that use of certain R$^2$ groups (e.g., sulfonyl groups such as —SO$_2$R$^{2a}$) may not require a transition metal catalyst (e.g., palladium catalyst as described above and herein) to reduce or eliminate the formation of a compound of formula 1-4-a, or a salt thereof.

In some embodiments, $R^2$ is —$SO_2R^{2a}$, wherein $R^{2a}$ is an optionally substituted $C_{1-6}$ aliphatic or aryl. In some embodiments, $R^{2a}$ is optionally substituted $C_{1-6}$ aliphatic or aryl. In some embodiments, $R^{2a}$ is optionally substituted $C_{1-6}$ aliphatic. In some embodiments, $R^{2a}$ is methyl. In some embodiments, $R^{2a}$ is $C_{1-6}$ aliphatic optionally substituted with halogen. In some embodiments, $R^{2a}$ is $C_{1-6}$ aliphatic optionally substituted with fluoro. In some embodiments, $R^{2a}$ is —$CF_3$. In some embodiments, $R^{2a}$ is optionally substituted aryl. In some embodiments, $R^{2a}$ is phenyl. In some embodiments, $R^{2a}$ a is tolyl. In some embodiments, $R^{2a}$ is p-tolyl. In some embodiments, $R^{2a}$ is methyl, —$CF_3$, or p-tolyl.

In some embodiments, $R^2$ is -$SO_2CH_3$. In some embodiments, $R^2$ is —$SO_2CF_3$. In some embodiments, $R^2$ is —$SO_2$(p-tolyl).

In some embodiments, $R^2$-X is tosyl chloride. In some embodiments, $R^2$-X is mesyl chloride. In some embodiments, $R^2$-X is triflyl chloride.

In some embodiments, the conditions suitable to afford a compound of formula 1-4, or a salt thereof, comprise an activating agent. In some embodiments, an activating agent is a base. In some embodiments, an activating agent is a strong organic base. In some embodiments, an activating agent is 4-dimethylaminopyridine (DMAP), imidazole, 1-methylimidazole, pyridine, lutidine, 1,8-diazabicyclo[5.4.0]undec-7-ene (DBU), 1,5-dizazabicyclo[4.3.0]non-5-ene (DBN), or 1,4-diazabicyclo[2.2.2]octane (DABCO). In some embodiments, an activating agent is 4-dimethylaminopyridine (DMAP). In some embodiments, an activating agent is imidazole. In some embodiments, an activating agent is 1-methylimidazole. In some embodiments, an activating agent is pyridine. In some embodiments, an activating agent is lutidine. In some embodiments, an activating agent is 1,8-diazabicyclo[5.4.0]undec-7-ene (DBU). In some embodiments, an activating agent is 1,5-dizazabicyclo[4.3.0]non-5-ene (DBN). In some embodiments, an activating agent is 1,4-diazabicyclo[2.2.2]octane (DABCO).

In some embodiments, the conditions suitable to afford a compound of formula 1-4, or a salt thereof, do not comprise a transition metal catalyst. In some embodiments, the conditions suitable to afford a compound of formula 1-4, or a salt thereof, do not comprise a palladium catalyst (e.g., as described above and herein).

Step S-4 of Scheme 3

At step S-4, a compound of formula 1-4, or a salt thereof, is coupled to a mercaptoacetate ester of formula 1-4-a to afford a compound of formula I-a, or a salt thereof:

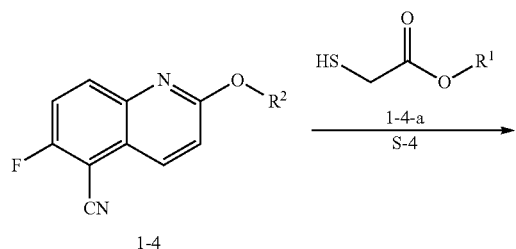

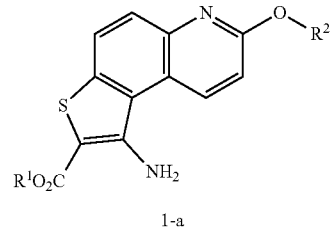

In some embodiments, at step S-4, a compound of formula I-a, or a salt thereof, is prepared by a method comprising the step of contacting a compound of formula 1-4, or a salt thereof, with a mercaptoacetate ester of formula 1-4-a. Accordingly, in some embodiments, at step S-4, a compound of formula I-a, or a salt thereof, is prepared by a method comprising:

(a) providing a compound of formula 1-4:

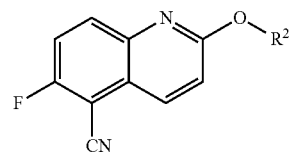

or a salt thereof; and (b) contacting the compound of formula 1-4 with a mercaptoacetate ester of formula 1-4-a:

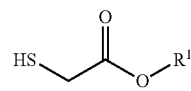

wherein $R^1$ is optionally substituted $C_{1-6}$ aliphatic;
under conditions suitable to form a compound of formula I-a, or a salt thereof.

In some embodiments, the conditions suitable to afford a compound of formula I-a, or a salt thereof, comprise a base. In some embodiments, the base is an alkoxide base. In some embodiments, an alkoxide base is selected from sodium methoxide (NaOMe) or sodium ethoxide (NaOEt). In some embodiments, the alkoxide base is NaOMe when $R^1$ is methyl. In some embodiments, the alkoxide base is NaOEt when $R^1$ is ethyl.

In some embodiments, compound 1-4, or a salt thereof, is coupled to a mercaptoacetate ester of formula 1-4-a in the presence of an alkoxide base.

In some embodiments, $R^1$ is optionally substituted $C_{1-4}$ aliphatic. In some embodiments, $R^1$ is optionally substituted $C_{1-2}$ aliphatic. In some embodiments, $R^1$ is selected from methyl, ethyl, and isopropyl. In some embodiments, $R^1$ is methyl.

Additionally or alternatively, in some embodiments, the present disclosure provides an improved synthesis of a compound of formula I-b:

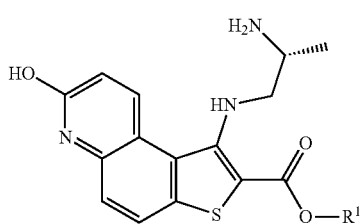

or a salt thereof, wherein:
R¹ is defined above and described herein.

Additionally or alternatively, in some embodiments, the present disclosure provides an improved synthesis of a compound of formula I-c:

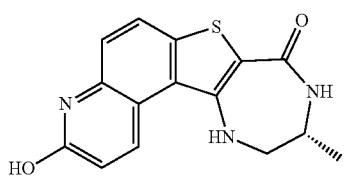

or a salt thereof.

In some embodiments, a compound of formula I-b, or a salt thereof, and/or a compound of formula I-c, or a salt thereof, are prepared according to Scheme 4:

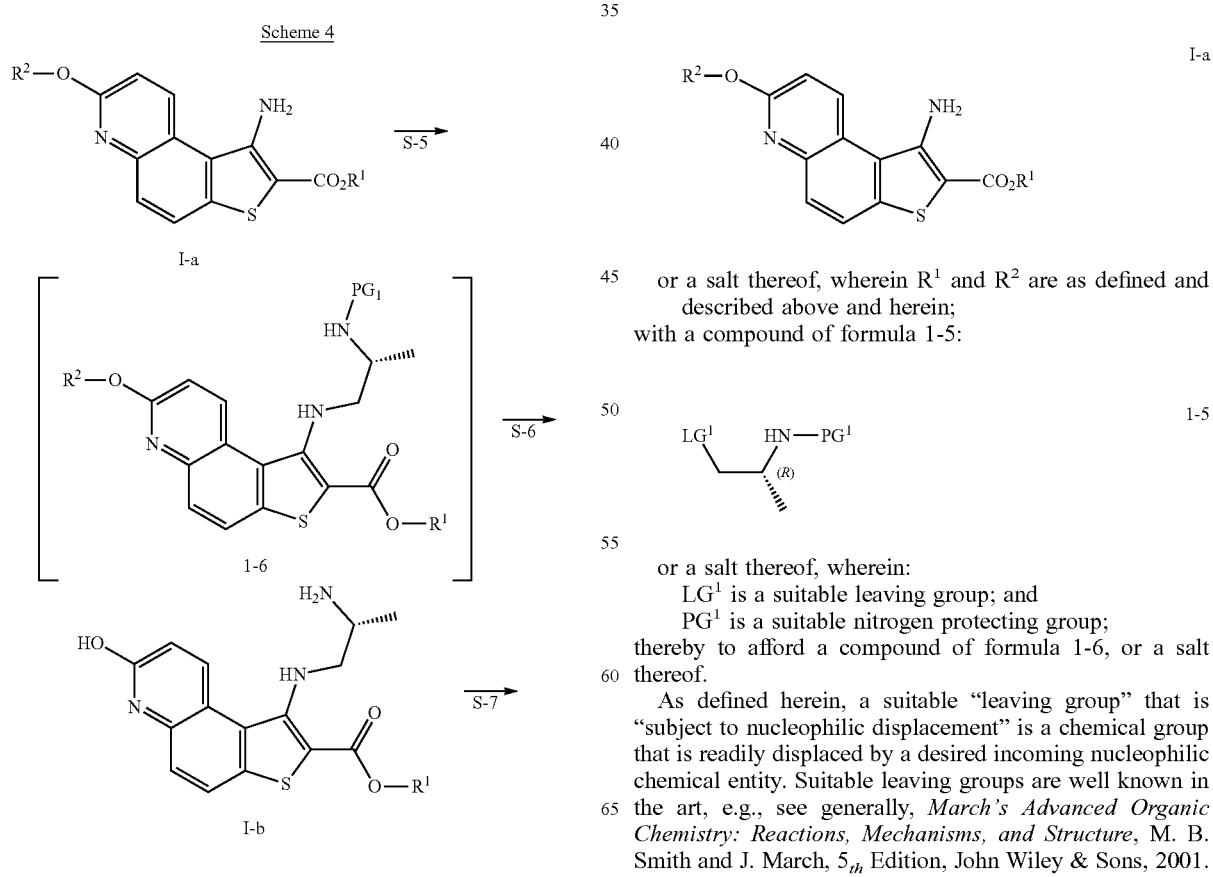

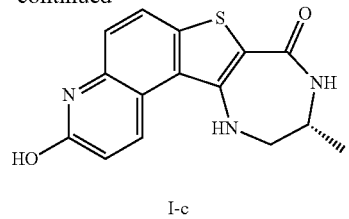

Step S-5 of Scheme 4

At step S-5 of Scheme 4, a compound of formula I-a is coupled with a compound of formula 1-5:

$$\text{1-5}$$

or a salt thereof, wherein LG¹ and PG¹ are as defined below and described herein to thereby afford a compound of formula 1-6.

In some embodiments, a compound of formula I-a is coupled to a compound of formula 1-5 via nucleophilic displacement of LG¹ by the amine of a compound of formula I-a. In some embodiments, at step S-5 of Scheme 4, a compound of formula 1-6 is prepared by a process comprising:

contacting a compound of formula I-a:

$$\text{I-a}$$

or a salt thereof, wherein R¹ and R² are as defined and described above and herein;

with a compound of formula 1-5:

$$\text{1-5}$$

or a salt thereof, wherein:
LG¹ is a suitable leaving group; and
PG¹ is a suitable nitrogen protecting group;
thereby to afford a compound of formula 1-6, or a salt thereof.

As defined herein, a suitable "leaving group" that is "subject to nucleophilic displacement" is a chemical group that is readily displaced by a desired incoming nucleophilic chemical entity. Suitable leaving groups are well known in the art, e.g., see generally, *March's Advanced Organic Chemistry: Reactions, Mechanisms, and Structure*, M. B. Smith and J. March, 5$_{th}$ Edition, John Wiley & Sons, 2001.

Such leaving groups include, but are not limited to, halogen, alkoxy, sulphonyloxy, optionally substituted alkylsulphonyloxy, optionally substituted alkenylsulfonyloxy, optionally substituted arylsulfonyloxy, phosphonate, sulfoxide, sulphone, and diazonium moieties. For the above mentioned "optionally substituted" moieties, the moieties may be optionally substituted with $C_{1-4}$ aliphatic, fluoro-substituted $C_{1-4}$ aliphatic, halogen, or nitro. Examples of suitable leaving groups include chloro, iodo, bromo, fluoro, sulfoxide, sulphone, methanesulfonyloxy (mesyloxy), tosyloxy, triflyloxy, benzenesulfonyloxy, nitro-phenyl sulfonyloxy (nosyloxy), and bromophenylsulfonyloxy (brosyloxy).

In some embodiments, $LG^1$ is a suitable leaving group as defined above and herein. In some embodiments, $LG^1$ is a sulfonate ester. In some embodiments of formula 1-5, $LG^1$ and the nitrogen atom cyclize to form a sulfamate. Accordingly, in some embodiments, a compound of formula 1-5 has a structure of formula 1-5-a:

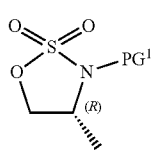

or a salt thereof, wherein $PG^1$ is as defined above and described herein.

A $PG^1$ group of a compound of formula 1-5 or 1-5-a is a suitable nitrogen protecting group. Various methods and conditions for protecting amines are known in the chemical arts. For example, suitable nitrogen protecting groups are well known in the art and include those described in detail in Protecting Groups in Organic Synthesis, T. W. Green and P. G. M. Wuts, $3_{rd}$ edition, John Wiley & Sons, 1999, the entirety of which is incorporated herein by reference. Suitable nitrogen protecting groups, taken with the —NH— moiety to which it is attached, include, but are not limited to, aralkylamines, carbamates, allyl amines, amides, and the like. Examples of $PG^1$ groups of a compound of formula 1-5 or 1-5-a include t-butyloxycarbonyl (Boc), p-methoxybenzyloxy carbonyl (PMB), ethyloxycarbonyl, methyloxycarbonyl, trichloroethyloxycarbonyl, allyloxycarbonyl (Alloc), benzyloxocarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like.

In some embodiments, $PG^1$ is t-butyloxycarbonyl (Boc). In certain embodiments, $PG^1$ is Boc, and the reagent used to install $PG^1$ is di-tert-butyl dicarbonate.

In some embodiments, step S-5 of Scheme 4 is conducted in the presence of a base. In some embodiments, the base is an inorganic base. In some embodiments, the base is NaH.

In some embodiments, the base is LiOR, NaOR, or KOR, wherein R is as defined above and described herein. In some embodiments, the base is an alkoxide. For instance, in some embodiments, the base is LiOR, NaOR, or KOR, wherein R is $C_{1-6}$ aliphatic or aryl. In some embodiments, the base is an alkoxide such as LiOR, NaOR, or KOR, wherein R is $C_{1-6}$ aliphatic. In some embodiments, the base is an alkoxide such as LiOR, NaOR, or KOR, wherein R is methyl. In some embodiments, the base is an alkoxide such as LiOR, NaOR, or KOR, wherein R is ethyl. In some embodiments, the base is an alkoxide such as LiOR, NaOR, or KOR, wherein R is propyl. In some embodiments, the base is an alkoxide such as LiOR, NaOR, or KOR, wherein R is butyl. In some embodiments, the base is an alkoxide such as LiOR, NaOR, or KOR, wherein R is pentyl. In some embodiments, the base is an alkoxide such as LiOR, NaOR, or KOR, wherein R is hexyl. In some embodiments, the base is LiOMe. In some embodiments, the base is NaOMe. In some embodiments, the base is KOMe. In some embodiments, the base is LiOEt. In some embodiments, the base is NaOEt. In some embodiments, the base is KOEt. In some embodiments, the base is LiOtBu. In some embodiments, the base is NaOtBu. In some embodiments, the base is KOtBu.

In some embodiments, step S-5 of Scheme 4 is conducted in the presence of a solvent. In some embodiments, the solvent comprises N-methyl-2-pyrrolidone (NMP). In some embodiments, the solvent comprises DMF. In some embodiments, the solvent comprises THF.

In some embodiments, step S-5 of Scheme 4 is conducted in the presence of a base and a solvent. In some embodiments, the base is LiOtBu and the solvent comprises NMP. In some embodiments, the base is NaH and the solvent comprises DMF.

In some embodiments, step S-5 of Scheme 4 comprises mixing a compound of formula I-a, a compound of formula 1-5 (e.g., a compound of formula 1-5-a), and a solvent (e.g., NMP). In some embodiments, the resulting mixture is cooled to a lower temperature. In some embodiments, a lower temperature is between about 0° C. and −25° C. In some embodiments, a lower temperature is between about −10° C. and −15° C. In some embodiments, a base (e.g., LiOtBu) in a solvent (e.g., THF) is added. In some embodiments, the base (e.g., LiOtBu) in a solvent (e.g., THF) is added over a period of about 90 mins. In some embodiments, a resulting reaction mixture is agitated for a period of time. In some embodiments, the period of time is between about 15 mins to about 60 mins. In some embodiments, the period of time is about 30 mins. In some embodiments, while a resulting reaction mixture is agitated, the temperature is maintained.

In some embodiments, a compound of formula 1-6 is taken into step S-6 of Scheme 4 without being isolated. In some embodiments, a compound of formula 1-6 is isolated after step S-5 of Scheme 4.

In some embodiments of formula 1-6, $R^2$ is benzyl. In some embodiments of formula 1-6, $R^2$ is tosyl (i.e., —SO$_2$(p-tolyl)). In some embodiments of formula 1-6, $R^1$ is $C_{1-6}$ aliphatic. In some such embodiments, $R^1$ is methyl.

In some embodiments, the present invention provides a method for preparing a compound of formula 1-6:

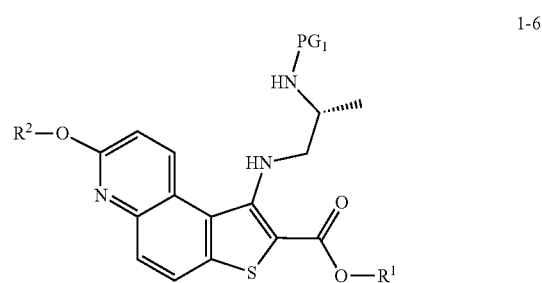

or a salt thereof, wherein:
PG$^1$ is a suitable nitrogen protecting group;
$R^1$ is optionally substituted $C_{1-6}$ aliphatic;
$R^2$ is optionally substituted $C_{1-6}$ aliphatic or —SO$_2$R$^{2a}$; and $R^{2a}$ is an optionally substituted $C_{1-6}$ aliphatic or aryl;

comprising the step of reacting a compound of formula I-a:

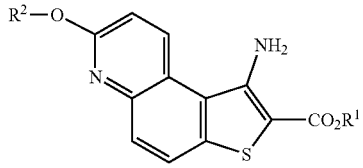

or a salt thereof;

with a compound of formula 1-5:

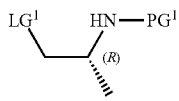

or a salt thereof, wherein:

$PG^1$ is a suitable nitrogen protecting group;

$LG^1$ is a suitable leaving group; and under suitable reaction conditions to afford a compound of formula 1-6, or a salt thereof.

In some embodiments, the present invention provides a method for preparing a compound of formula 1-6:

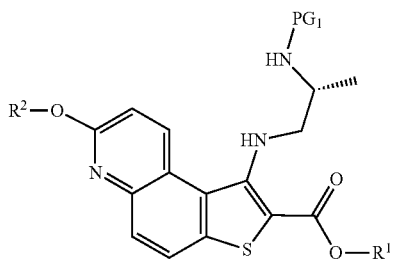

or a salt thereof, wherein:

$PG^1$ is a suitable nitrogen protecting group;

$R^1$ is optionally substituted $C_{1-6}$ aliphatic;

$R^2$ is optionally substituted $C_{1-6}$ aliphatic or $-SO_2R^{2a}$; and $R^{2a}$ is an optionally substituted $C_{1-6}$ aliphatic or aryl;

comprising the step of reacting a compound of formula I-a

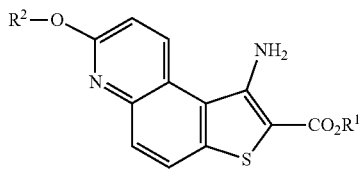

or a salt thereof, with a compound of formula 1-5-a:

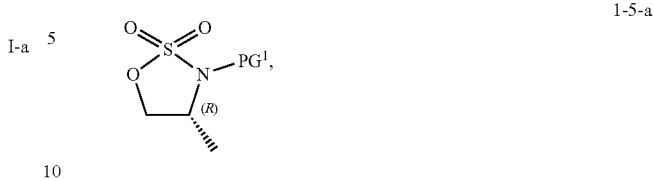

or a salt thereof, wherein $PG^1$ is a suitable nitrogen protecting group; under suitable reaction conditions to thereby afford the compound of formula 1-6, or a salt thereof.

Step S-6 of Scheme 4

At step S-6 of Scheme 4, a compound of formula 1-6, or a salt thereof, is deprotected to afford a compound of formula I-b, or a salt thereof. In some embodiments, at step S-6 of Scheme 4, a compound of formula I-b, or a salt thereof, is prepared by a process comprising:

contacting a compound of formula 1-6:

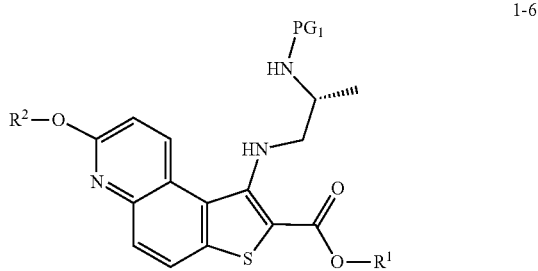

or a salt thereof, wherein:

$PG^1$ is a suitable nitrogen protecting group;

$R^1$ is optionally substituted $C_{1-6}$ aliphatic;

$R^2$ is optionally substituted $C_{1-6}$ aliphatic or $-SO_2R^{2a}$; and $R^{2a}$ is an optionally substituted $C_{1-6}$ aliphatic or aryl;

with an acid, to thereby afford the compound of formula I-b, or a salt thereof.

$PG^1$ is as described above and defined herein. Various methods and conditions for deprotecting amines (e.g., $PG^1$) are known in the chemical arts. For example, methods and conditions for deprotecting amines are well known in the art and include those described in detail in *Protecting Groups in Organic Synthesis*, T. W. Green and P. G. M. Wuts, $3^{rd}$ edition, John Wiley & Sons, 1999, the entirety of which is incorporated herein by reference. In some embodiments of formula 1-6, $PG^1$ is Boc.

In some embodiments, $PG^1$ of formula 1-6 is removed by acid. In some embodiments, a wide variety of acids are useful for removing nitrogen protecting groups that are acid labile. In some embodiments, the acid is a Lewis acid. In some embodiments, the acid is a Bronsted acid.

In some embodiments, the acid is an inorganic acid. In some embodiments, the acid is HF, HBr, HCl, $H_2S$, $HNO_3$, $H_3PO_4$, $H_2SO_4$, $H_3BO_3$, $HClO_4$, or HI. In some embodiments, the acid is HCl. In some embodiments, the inorganic acid is in a solvent. In some embodiments, the inorganic acid is in water. In some embodiments, the inorganic acid is in isopropanol. In some embodiments, HCl is in isopropanol. In some embodiments, the acid is an organic acid. In some embodiments, the acid is lactic acid, acetic acid, formic acid, citric acid, oxalic acid, uric acid, malic acid, tartaric acid, trifluoroacetic acid, methanesulfonic acid, benzenesulfonic acid, or p-toluenesulfonic acid (PTSA). $R^2$ is as described above and defined herein. In some embodiments, $R^2$ is benzyl. In some embodiments, $R^2$ is tosyl (i.e., —$SO_2$(p-tolyl)). In some embodiments, $R^2$ of a compound of formula 1-6 is removed by acid. In some embodiments, the acid is an inorganic acid. In some embodiments, the acid is HF, HBr, HCl, $H_2S$, $HNO_3$, $H_3PO_4$, $H_2SO_4$, $H_3BO_3$, $HClO_4$, or HI. In some embodiments, the acid is an organic acid. In some embodiments, the acid is lactic acid, acetic acid, formic acid, citric acid, oxalic acid, uric acid, malic acid, tartaric acid, trifluoroacetic acid, methanesulfonic acid, benzenesulfonic acid, or p-toluenesulfonic acid (PTSA). In some embodiments, a wide variety of acids are useful for removing oxygen protecting groups that are acid labile. In some embodiments, the acid is a Lewis acid. In some embodiments, the acid is a Bronsted acid.

$R^2$ is as described above and defined herein. In some embodiments, $R^2$ is benzyl. In some embodiments, $R^2$ is tosyl (i.e., —$SO_2$(p-tolyl)). In some embodiments, $R^2$ of a compound of formula 1-6 is removed by acid. In some embodiments, a wide variety of acids are useful for removing oxygen protecting groups that are acid labile. In some embodiments, the acid is a Lewis acid. In some embodiments, the acid is a Bronsted acid.

In some embodiments, $R^2$ of a compound of formula 1-6 is removed with a sulfonic acid, for example methanesulfonic acid, benzenesulfonic acid (BSA), or p-toluenesulfonic acid (PTSA). In some embodiments, $R^2$ of a compound of formula 1-6 is removed with methanesulfonic acid. In some embodiments, $R^2$ of a compound of formula 1-6 is removed with BSA. In some embodiments, $R^2$ of a compound of formula 1-6 is removed with PTSA.

In some embodiments, step S-6 of Scheme 4 is conducted in the presence of a solvent. In some embodiments, the solvent comprises a polar protic solvent. In some embodiments, the solvent comprises methanol. In some embodiments, the solvent comprises a polar aprotic solvent. In some embodiments, the solvent comprises MeCN. In some embodiments, the solvent comprises a polar protic solvent and a polar aprotic solvent. In some embodiments, the solvent comprises methanol and MeCN.

In some embodiments, a compound of formula 1-6 is isolated after step S-5 of Scheme 4. In some embodiments, step S-6 of Scheme 4 comprises mixing a compound of formula 1-6 and an acid (e.g., MSA) in a solvent (e.g., MeCN) and adding water. In some embodiments, the reaction mixture is agitated for an amount of time. In some embodiments, the reaction mixture is agitated for between about 5 mins and about 1 hr. In some embodiments, the reaction mixture is agitated for about 15 mins. In some embodiments, the reaction mixture is additionally heated and agitated for an amount of time. In some embodiments, the reaction mixture is additionally heated to reflux and agitated for an amount of time. In some embodiments, the reaction mixture is additionally heated to reflux and agitated for between about 6 hr and about 36 hr. In some embodiments, the reaction mixture is additionally heated to reflux and agitated for about 20 h.

In some embodiments, at step S-6 of Scheme 4, a compound of formula I-b is prepared in a "one pot" reaction, such "one pot" reaction comprising coupling a compound of formula I-a with a compound of formula 1-5 to thereby afford a compound of formula 1-6, followed by in situ deprotection, thereby resulting in a compound of formula I-b. For instance, in some embodiments, step S-6 of Scheme 4 comprises an addition of a solvent (e.g., MeCN) to the crude product of step S-5 of Scheme 4. In some embodiments, step S-6 of Scheme 4 comprises an addition of an acid (e.g., MSA or BSA) and water to the crude product of step S-5 of Scheme 4. In some embodiments, an addition of an acid (e.g., MSA or BSA) is performed dropwise. In some embodiments, an addition of an acid (e.g., MSA or BSA) is performed at between about 65° C. and 70° C. In some embodiments, the reaction is agitated for an amount of time. In some embodiments, the reaction is agitated for between about 6 hr and about 24 hr. In some embodiments, the reaction is agitated for an amount of time. In some embodiments, the reaction is agitated for about 16 h.

In some embodiments, each of $PG^1$ and $R^2$ is removed by an acid. In some embodiments, the acid is an inorganic acid. In some embodiments, the acid is HF, HBr, HCl, $H_2S$, $HNO_3$, $H_3PO_4$, $H_2SO_4$, $H_3BO_3$, $HClO_4$, or HI. In some embodiments, the acid is an organic acid. In some embodiments, the acid is lactic acid, acetic acid, formic acid, citric acid, oxalic acid, uric acid, malic acid, tartaric acid, trifluoroacetic acid, methanesulfonic acid, benzenesulfonic acid, or p-toluenesulfonic acid (PTSA). In some embodiments, each of $PG^1$ and $R^2$ is removed by HCl. In some embodiments, each of $PG^1$ and $R^2$ is removed by BSA. In some embodiments, each of $PG^1$ and $R^2$ is removed by MSA. In some embodiments, each of $PG^1$ and $R^2$ is removed by p-toluenesulfonic acid.

In some embodiments, the present disclosure provides the recognition that certain salt forms of a compound of formula I-b display improved physical and/or chemical properties, which may contribute to improved yields and control impurities leading to a robust process, particularly when scaling-up the synthesis. In some embodiments, a compound of formula I-b is isolated as a salt. In some embodiments, a compound of formula I-b is isolated as an HF, HBr, HCl, $H_2S$, $HNO_3$, $H_3PO_4$, $H_2SO_4$, $H_3BO_3$, $HClO_4$, or HI salt. In some embodiments, a compound of formula I-b is isolated as a lactic acid, acetic acid, formic acid, citric acid, oxalic acid, uric acid, malic acid, tartaric acid, trifluoroacetic acid, methanesulfonic acid, benzenesulfonic acid, or p-toluenesulfonic acid (PTSA) salt. In some embodiments, a compound of formula I-b is isolated as an HCl salt. In some embodiments, a compound of formula I-b is isolated as a BSA salt. In some embodiments, a compound of formula I-b is isolated as a MSA salt. In some embodiments, a compound of formula I-b is isolated as a p-toluenesulfonic acid salt.

In some embodiments, the present invention provides a method for preparing a compound of formula I-b:

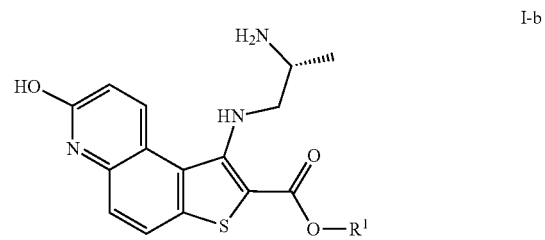

or a salt thereof, wherein:

$R^1$ is optionally substituted $C_{1-6}$ aliphatic;

comprising the step of reacting a compound of formula 1-6:

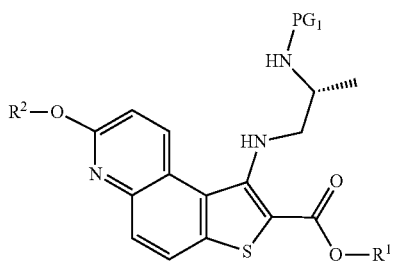

or a salt thereof, wherein:
$R^1$ is optionally substituted $C_{1-6}$ aliphatic;
$PG^1$ is a suitable nitrogen protecting group;
$R^2$ is optionally substituted $C_{1-6}$ aliphatic or —$SO_2R^{2a}$; and
$R^{2a}$ is an optionally substituted $C_{1-6}$ aliphatic or aryl;
under suitable reaction conditions to afford the compound of formula I-b, or a salt thereof.

In some embodiments, the present invention provides a method for preparing a compound of formula I-b:

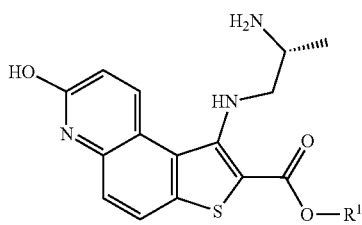

or a salt thereof, wherein:
$R^1$ is optionally substituted $C_{1-6}$ aliphatic;
comprising the steps of:
(a) reacting a compound of formula I-a:

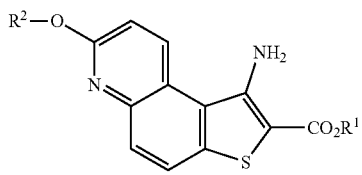

or a salt thereof, wherein:
$R^1$ is optionally substituted $C_{1-6}$ aliphatic;
$R^2$ is optionally substituted $C_{1-6}$ aliphatic or —$SO_2R^{2a}$; and
$R^{2a}$ is an optionally substituted $C_{1-6}$ aliphatic or aryl;
with a compound of formula 1-5:

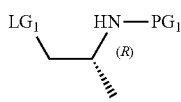

or a salt thereof, wherein:
$PG^1$ is a suitable nitrogen protecting group; and
$LG^1$ is a suitable leaving group;
under suitable reaction conditions to afford a compound of formula 1-6:

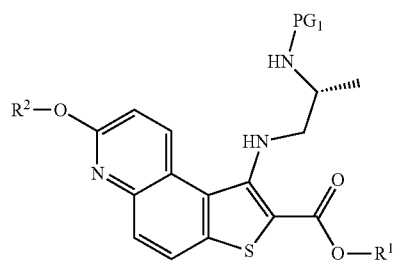

or a salt thereof; and
(b) reacting the compound of formula 1-6 under suitable reaction conditions to afford the compound of formula I-b, or a salt thereof.

In some embodiments, the present invention provides a method for preparing a compound of formula I-b:

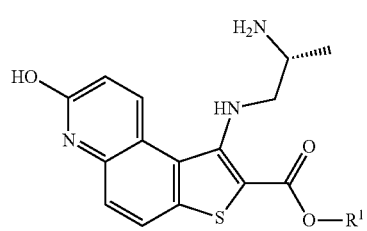

or a salt thereof, wherein:
$R^1$ is optionally substituted $C_{1-6}$ aliphatic;
comprising the steps of:
(a) reacting a compound of formula 1-7:

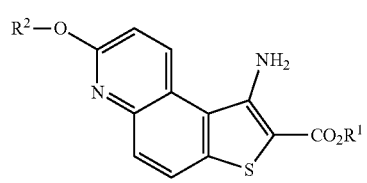

or a salt thereof, wherein:
$R^1$ is optionally substituted $C_{1-6}$ aliphatic;
$R^2$ is optionally substituted $C_{1-6}$ aliphatic or —$SO_2R^{2a}$; and
$R^{2a}$ is an optionally substituted $C_{1-6}$ aliphatic or aryl;
with a compound of formula 1-5-a:

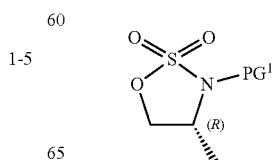

or a salt thereof, wherein:
PG¹ is a suitable nitrogen protecting group; under suitable reaction conditions to afford a compound of formula 1-6:

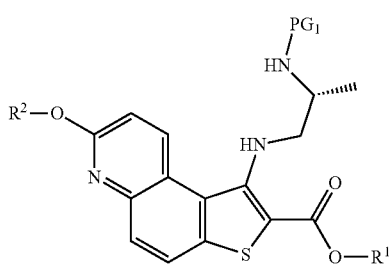

or a salt thereof; and
(b) reacting the compound of formula 1-6 under suitable reaction conditions to afford the compound of formula I-b, or a salt thereof.

Step S-7 of Scheme 4

At step S-7 of Scheme 4, a compound of formula I-b undergoes cyclization to form a compound of formula I-c. In some embodiments, step S-7 of Scheme 4 is conducted in the presence of base. In some embodiments, the present invention provides a method for preparing a compound of formula I-c:

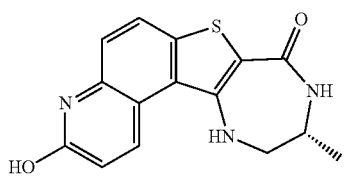

or a salt thereof,
comprising the steps of
(a) providing a compound of formula I-b

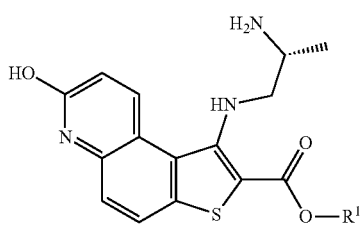

or a salt thereof, where $R^1$ is as described above and herein; and
(b) reacting the compound of formula I-b, or a salt thereof, with a base,
to thereby afford the compound of formula I-c, or a salt thereof.

In some embodiments, the base is an inorganic base. In some embodiments, the base is an alkali hydroxide. In some embodiments, the base is LiOH. In some embodiments, the base is NaOH. In some embodiments, the base is KOH. In some embodiments, the base is a carbonate. In some embodiments, the base is $K_2CO_3$. In some embodiments, the base is $Na_2CO_3$. In some embodiments, the base is a bicarbonate. In some embodiments, the base is $KHCO_3$. In some embodiments, the base is $NaHCO_3$. In some embodiments, the base is a phosphate. In some embodiments, the base is $Na_3PO_4$. In some embodiments, the base is $K_3PO_4$.

In some embodiments, the base is LiOR, NaOR, or KOR, wherein R is as defined above and described herein. In some embodiments, the base is an alkoxide. For instance, in some embodiments, the base is LiOR, NaOR, or KOR, wherein R is $C_{1-6}$ aliphatic or aryl. In some embodiments, the base is an alkoxide such as LiOR, NaOR, or KOR, wherein R is $C_{1-6}$ aliphatic. In some embodiments, the base is an alkoxide such as LiOR, NaOR, or KOR, wherein R is methyl. In some embodiments, the base is an alkoxide such as LiOR, NaOR, or KOR, wherein R is ethyl. In some embodiments, the base is an alkoxide such as LiOR, NaOR, or KOR, wherein R is propyl. In some embodiments, the base is an alkoxide such as LiOR, NaOR, or KOR, wherein R is butyl. In some embodiments, the base is an alkoxide such as LiOR, NaOR, or KOR, wherein R is pentyl. In some embodiments, the base is an alkoxide such as LiOR, NaOR, or KOR, wherein R is hexyl. In some embodiments, the base is LiOMe. In some embodiments, the base is NaOMe. In some embodiments, the base is KOMe. In some embodiments, the base is LiOEt. In some embodiments, the base is NaOEt. In some embodiments, the base is KOEt. In some embodiments, the base is LiOtBu. In some embodiments, the base is NaOtBu. In some embodiments, the base is KOtBu.

In some embodiments, the base is an organic base. In some embodiments, the base is an amine base. In some embodiments, the base is trimethylamine. In some embodiments, the base is diisopropylethylamine (DIEA). In some embodiments, the base is triethylamine. In some embodiments, the base is DBU.

In some embodiments, step S-7 is conducted in the presence of a solvent. In some embodiments, the solvent comprises a polar protic solvent. In some embodiments, the solvent comprises methanol. In some embodiments, a solvent comprises DMSO, dimethylacetamide (DMAc), dimethylformamide (DMF), N-methylpyrrolidone (NMP), 1,3-dimethyl-3,4,5,6-tetrahydro-2(1H)-pyrimidinone (DMPU), sulfolane, or anisole. In some embodiments, the solvent comprises DMSO. In some embodiments, a solvent comprises dimethylacetamide (DMAc). In some embodiments, a solvent comprises dimethylformamide (DMF). In some embodiments, a solvent comprises N-methylpyrrolidone (NMP). In some embodiments, a solvent comprises 1,3-dimethyl-3,4,5,6-tetrahydro-2(1H)-pyrimidinone (DMPU). In some embodiments, a solvent comprises sulfolane. In some embodiments, a solvent comprises anisole.

In some embodiments, step S-7 is conducted under inert conditions (e.g., under nitrogen gas). In some embodiments, step S-7 is conducted under conditions that comprise reduced amounts of $O_2$ gas, e.g., as compared to air. In some embodiments, $O_2$ gas is present in an amount of less than about 1,000 ppm. In some embodiments, $O_2$ gas is present in an amount of less than about 800 ppm. In some embodiments, $O_2$ gas is present in an amount of less than about 700 ppm. In some embodiments, $O_2$ gas is present in an amount of less than about 600 ppm. In some embodiments, $O_2$ gas is present in an amount of less than about 500 ppm. In some embodiments, $O_2$ gas is present in an amount of less than about 400 ppm. In some embodiments, $O_2$ gas is present in an amount of less than about 300 ppm. In some embodiments, $O_2$ gas is present in an amount of less than about 200 ppm. In some embodiments, $O_2$ gas is present in an amount of less than about 100 ppm. In some embodiments, the amount of $O_2$ gas is monitored, e.g., by a Teledyne $O_2$ monitor system.

In some embodiments, step S-7 comprises mixing a compound of formula I-b and a solvent (e.g., DMSO). In some embodiments, step S-7 comprises an addition of a base (e.g., DBU). In some embodiments, the base (e.g., DBU) is added dropwise. In some embodiments, the base (e.g., DBU) is added at a rate to maintain the temperature of the mixture. In some embodiments, the base (e.g., DBU) is added at room temperature. In some embodiments, the base (e.g., DBU) is added to the mixture of a compound of formula I-b and a solvent (e.g., methanol) at a temperature between about 10° C. and about 45° C. In some embodiments, the base (e.g., DBU) is added to the mixture of a compound of formula I-b and a solvent (e.g., methanol) at a temperature between about 20° C. and about 30° C. In some embodiments, the base (e.g., DBU) is added to the mixture of a compound of formula I-b and a solvent (e.g., methanol) at a temperature between about 20° C. and about 25° C. In some embodiments, the reaction mixture is heated to an elevated temperature and agitated for a period of time. In some embodiments, an elevated temperature is between about 50° C. and about 85° C. In some embodiments, an elevated temperature is between about 60° C. and about 70° C. In some embodiments, an elevated temperature is between about 60° C. and about 65° C. In some embodiments, a period of time is between about 1 hr and about 8 hrs. In some embodiments, a period of time is between about 1 hr and about 6 hrs. In some embodiments, a period of time is between about 2 hrs and about 6 hrs. In some embodiments, a period of time is between about 3 hrs and about 5 hrs. In some embodiments, a period of time is about 4 hrs. In some embodiments, a period of time is greater than 8 hrs. In some embodiments, a period of time is until the starting material is consumed, e.g., as monitored by HPLC.

In some embodiments, after the cyclization reaction is performed, the crude product of step S-7 undergoes crystallization prior to be isolated. In some embodiments, the present disclosure provides the recognition that, after cyclization, a crystallization step may provide a higher yield of a compound of formula I-c, or a salt thereof, and/or provide the compound of formula I-c, or a salt thereof, in a particular form that may display improved physical and/or chemical properties, in particular when the synthesis is scaled-up. In some embodiments, such improved physical and/or chemical properties may contribute to an improved yield when synthesizing Compound I.

For example, the synthesis of Compound I described in the '203 publication discloses a 2-step process for producing compound M of Scheme 2, where compound M is first provided as a methanol solvate and then converted to an unsolvated form, which was isolated. See, e.g., the '203 publication at paragraph [0291]. However, without wishing to be bound to a particular theory, such reaction conditions required use of methanol as the solvent, and the reaction stalled at about 98% conversion and produced methanol solvate of compound M of Scheme 2, which led to impurities and destroyed some of the starting material. To improve the conversion of starting material to compound M of Scheme 2, the '203 publication discloses that, after isolating the methanol solvent of compound M of Scheme 2, the methanol solvate was subjected to further reaction conditions (e.g., with MeCN and DBU) to convert the methanol solvate to an unsolvated form of compound M of Scheme 2, and push the reaction conversion above 99%. In some embodiments, the present disclosure provides the recognition that use of a different solvent to perform the cyclization of step S-7 and/or performing a subsequent crystallization step, may improve the yield of the desired form of a compound of formula I-c, or a salt thereof, e.g., by allowing the reaction to be performed in a single process and avoid isolating the methanol solvate, thereby eliminating the need to convert the resulting solvate to an unsolvated form of a compound of formula I-c, or a salt thereof.

In some embodiments, step S-7 comprises a crystallization step. In some embodiments, such a crystallization step provides an unsolvated form of a compound of formula I-c, or a salt thereof. In some embodiments, step S-7 comprises crystallization. It will be understood that, in some embodiments, crystallization involves the addition of a secondary solvent (e.g., an antisolvent) to a primary solvent to reduce solubility of the solute (e.g., compound of formula I-c or a salt thereof). In some embodiments, step S-7 comprises a crystallization, which comprises the following steps:
(a) providing the compound of formula I-c, or a salt thereof, in a primary solvent to form a primary mixture;
(b) adding a secondary solvent to the primary mixture to form a secondary mixture 1;
(c) optionally adding a seed crystal to the secondary mixture 1;
(d) optionally aging the secondary mixture 1;
(e) optionally adding additional secondary solvent to the secondary mixture to form a secondary mixture 2;
(f) optionally agitating the secondary mixture 2;
(g) optionally aging the secondary mixture 2;
(h) filtering the secondary mixture 2; and
(i) optionally washing the filtered crystals and/or drying under vacuum.

In some embodiments, the crystallization comprises step (a). In some embodiments, the crystallization comprises step (b). In some embodiments, the crystallization comprises step (c). In some embodiments, the crystallization comprises step (d). In some embodiments, the crystallization comprises step (e). In some embodiments, the crystallization comprises step (f). In some embodiments, the crystallization comprises step (g). In some embodiments, the crystallization comprises step (h). In some embodiments, the crystallization comprises step (i). In some embodiments, the crystallization comprises at least steps (a) and (b). In some embodiments, the crystallization comprises at least steps (a), (b), and (h). In some embodiments, the crystallization comprises at least steps (a), (b), and (d). In some embodiments, the crystallization comprises at least steps (a), (b), (d), and (h). In some embodiments, the crystallization comprises steps (a)-(d). In some embodiments, the crystallization comprises steps (a)-(d). In some embodiments, the crystallization comprises steps (a)-(d) and (h). In some embodiments, the crystallization comprises steps (a)-(g). In some embodiments, the crystallization comprises steps (a)-(h). In some embodiments, the crystallization comprises steps (a)-(i).

In some embodiments, the crystallization comprises at least steps (a), (b), and (i). In some embodiments, the crystallization comprises at least steps (a), (b), (h), and (i). In some embodiments, the crystallization comprises at least steps (a), (b), (d), and (i). In some embodiments, the crystallization comprises at least steps (a), (b), (d), (h), and (i). In some embodiments, the crystallization comprises steps (a)-(d) and (i). In some embodiments, the crystallization comprises steps (a)-(d), (h), and (i). In some embodiments, the crystallization comprises steps (a)-(g) and (i).

In some embodiments, the crystallization step of S-7 comprises (a) providing the compound of formula I-c, or a salt thereof, in a primary solvent to form a primary mixture. In some embodiments, the crude product of step S-7 (i.e., a compound of formula I-c, or a salt thereof) is provided in a primary solvent (e.g., the same solvent that the reaction was performed). In some embodiments, the primary solvent is the same solvent where a compound of formula I-b, or a salt thereof, is reacted to form a compound of formula I-c, or a salt thereof In some embodiments, a primary solvent is or comprises a polar protic solvent. In some embodiments, a primary solvent is or comprises methanol. In some embodiments, a primary solvent is or comprises DMSO, dimethylacetamide (DMAc), dimethylformamide (DMF), N-methylpyrrolidone (NMP), 1,3-dimethyl-3,4,5,6-tetrahydro-2(1H)-pyrimidinone (DMPU), sulfolane, or anisole. In some embodiments, a primary solvent is or comprises DMSO. In some embodiments, a primary solvent is or comprises dimethylacetamide (DMAc). In some embodiments, a primary solvent is or comprises dimethylformamide (DMF). In some embodiments, a primary solvent is or comprises N-methylpyrrolidone (NMP). In some embodiments, a primary solvent is or comprises 1,3-dimethyl-3,4,5,6-tetrahydro-2(1H)-pyrimidinone (DMPU). In some embodiments, a primary solvent is or comprises sulfolane. In some embodiments, a primary solvent is or comprises anisole. In some embodiments, a primary solvent is present at an amount of between about 4.0 mL/g of solute and about 8.0 mL/g solute. In some embodiments, a primary solvent is present at an amount of between about 4.0 mL/g solute and about 8.0 mL/g solute. In some embodiments, a primary solvent is present at an amount of between about 5.0 mL/g solute and about 8.0 mL/g solute. In some embodiments, a primary solvent is present at an amount of between about 4.0 mL/g solute and about 6.0 mL/g solute. In some embodiments, a primary solvent is present at an amount of between about 5.0 mL/g solute and about 6.0 mL/g solute. In some embodiments, a primary solvent is present at an amount of about 4.0, 4.5, 5.0, 5.5, 6.0, 6.5, or 7.0 mL/g solute.

In some embodiments, the crystallization step of S-7 comprises step (b) adding a secondary solvent to the primary mixture to form a secondary mixture 1. In some embodiments, a secondary solvent is or comprises a polar solvent. In some embodiments, a secondary solvent is or comprises a polar aprotic solvent. In some embodiments, a secondary solvent is or comprises a polar protic solvent. In some embodiments, a secondary solvent is a non-polar solvent. In some embodiments, a secondary solvent is or comprises acetone, MeCN, acetone, an alcohol (e.g., methanol, ethanol, n-propanol, isopropanol, or t-butanol), water, ethyl acetate, THF, or MBTE. In some embodiments, a secondary solvent is or comprises MeCN. In some embodiments, a secondary solvent is present at an amount of between about 1.0 mL/g solute and about 3.0 mL/g solute. In some embodiments, a secondary solvent is present at an amount of between about 1.5 mL/g solute and about 2.5 mL/g solute. In some embodiments, a secondary solvent is present at an amount of about 0.5, 1.0, 1.5, 2.0, 2.5, or 3.0 mL/g solute. In some embodiments, the secondary solvent is added dropwise. In some embodiments, the secondary solvent is added at an elevated temperature. In some embodiments, the elevated temperature is the same temperature that a compound of formula I-b, or a salt thereof, is reacted to form a compound of formula I-c, or a salt thereof. In some embodiments, an elevated temperature is between about 50° C. and about 85° C. In some embodiments, an elevated temperature is between about 60° C. and about 70° C. In some embodiments, an elevated temperature is between about 60° C. and about 65° C. In some embodiments, an elevated temperature is about 50, 55, 60, 65, 70, or 75° C.

In some embodiments, the crystallization step of S-7 comprises step (c) adding a seed crystal to the secondary mixture 1. In some embodiments, the seed crystal is added in an amount of between about 0.1 wt % and about 2 wt % of compound of formula I-b. In some embodiments, the seed crystal is added in an amount of between about 0.5 wt % and about 2 wt % of compound of formula I-b. In some embodiments, the seed crystal is added in an amount of between about 0.5 wt % and about 1.5 wt % of compound of formula I-b. In some embodiments, the seed crystal is added in an amount of between about 0.9 wt % and about 1.1 wt % of compound of formula I-b. In some embodiments, the seed crystal is added in an amount of about 0.5, 0.6, 0.7, 0.8, 0.9, 1.0, 1.1, 1.2, 1.3, 1.4, or 1.5 wt % wt % of compound of formula I-b. In some embodiments, a seed crystal is or comprises a compound of formula I-c, or a salt thereof, (e.g., where $R^1$ is methyl).

In some embodiments, the crystallization step of S-7 comprises step (d) aging the secondary mixture 1. In some embodiments, the secondary mixture 1 is aged for between about 1 hr and 8 hrs. In some embodiments, the secondary mixture 1 is aged for between about 1 hr and 4 hrs. In some embodiments, the secondary mixture 1 is aged for between about 1 hr and 3 hrs. In some embodiments, the secondary mixture 1 is aged for between about 1.5 hrs and 2.5 hrs. In some embodiments, the secondary mixture 1 is aged for about 0.5, 1.0, 1.5, 2.0, 2.5, 3.0, 3.5, or 4.0 hrs. In some embodiments, the secondary mixture 1 is aged at an elevated temperature. In some embodiments, the elevated temperature is the same temperature that a compound of formula I-b, or a salt thereof, is reacted to form a compound of formula I-c, or a salt thereof. In some embodiments, the elevated temperature is the same temperature that the secondary solvent is added. In some embodiments, an elevated temperature is between about 50° C. and about 85° C. In some embodiments, an elevated temperature is between about 60° C. and about 70° C. In some embodiments, an elevated temperature is between about 55° C. and about 65° C. In some embodiments, an elevated temperature is about 50, 55, 60, 65, 70, or 75° C.

In some embodiments, the crystallization step of S-7 comprises step (e) adding additional secondary solvent to the secondary mixture to form a secondary mixture 2. In some embodiments, additional secondary solvent is added in an amount of between about 1.0 mL/g solute and about 12 mL/g solute. In some embodiments, additional secondary solvent is added in an amount of between about 1.0 mL/g solute and about 10 mL/g solute. In some embodiments, additional secondary solvent is added in an amount of between about 1.0 mL/g solute and about 8.0 mL/g solute. In some embodiments, additional secondary solvent is added in an amount of between about 2.0 mL/g solute and about 6.5 mL/g solute. In some embodiments, additional secondary solvent is added in an amount of between about 3.0 mL/g solute and about 12.0 mL/g solute. In some embodiments, additional secondary solvent is added in an amount of between about 5.0 mL/g solute and about 12.0 mL/g solute. In some embodiments, additional secondary solvent is added in an amount of between about 2.5 mL/g solute and about 10 mL/g solute. In some embodiments, additional secondary solvent is added in an amount of between about 5.0 mL/g solute and about 7.0 mL/g solute. In some embodiments, additional secondary solvent is added in an amount of about 4.0, 4.5, 5.0, 5.5, 6.0, 6.5, 7.0, 7.5, 8.0, 8.5, or 9.0 mL/g solute. In some embodiments, additional secondary solvent is added over a period of time. In some embodiments, additional secondary solvent is added over the course of between about 1 hr and about 4 hrs. In some embodiments, additional secondary solvent is added over the course of between about 1 hr and about 3 hrs. In some embodiments, additional secondary solvent is added over the course of between about 1 hr and about 2 hrs. In some embodiments, additional secondary solvent is added over the course of between about 2 hrs and about 4 hrs. In some embodiments, additional secondary solvent is added over the course of between about 2 hrs and about 3 hrs. In some embodiments, additional secondary solvent is added over the course of about 1, 2, 3, or 4 hrs.

In some embodiments, the crystallization step of S-7 comprises step (f) agitating the secondary mixture 2. In some embodiments, the secondary mixture 2 is agitated for a period of time at a temperature. In some embodiments, the secondary mixture 2 is agitated for between about 1 hr and about 4 hrs. In some embodiments, the secondary mixture 2 is agitated for between about 2 hrs and about 4 hrs. In some embodiments, the secondary mixture 2 is agitated for between about 3 hrs and about 4 hrs. In some embodiments, the secondary mixture 2 is agitated for between about 1 hr and about 2 hrs. In some embodiments, the secondary mixture 2 is agitated for between about 1 hr and about 3 hrs. In some embodiments, the secondary mixture 2 is agitated for between about 2 hrs and about 3 hrs. In some embodiments, the secondary mixture 2 is agitated for about 1, 2, 3, or 4 hrs. In some embodiments, the secondary mixture 2 is agitated at an elevated temperature. In some embodiments, the elevated temperature is the same temperature at which a compound of formula I-b, or a salt thereof, is reacted to form a compound of formula I-c, or a salt thereof. In some embodiments, the elevated temperature is the same temperature at which the secondary solvent is added. In some embodiments, the elevated temperature is the same temperature at which the mixture comprising the compound of formula I-c, or a salt thereof, primary solvent, secondary solvent, and seed crystal is aged. In some embodiments, an elevated temperature is between about 50° C. and about 85° C. In some embodiments, an elevated temperature is between about 60° C. and about 70° C. In some embodiments, an elevated temperature is between about 60° C. and about 65° C. In some embodiments, an elevated temperature is about 50, 55, 60, 65, 70, or 75° C.

In some embodiments, the crystallization step of S-7 comprises step (g) aging the secondary mixture 2. In some embodiments, secondary mixture 2 is cooled to a temperature and aged for a period of time. In some embodiments, the secondary mixture 2 is aged at between about 0° C. and about 30° C. In some embodiments, the secondary mixture 2 is aged at between about 0° C. and about 25° C. In some embodiments, the secondary mixture 2 is aged at between about 0° C. and about 20° C. In some embodiments, the secondary mixture 2 is aged at between about 10° C. and about 30° C. In some embodiments, the secondary mixture 2 is aged at between about 20° C. and about 30° C. In some embodiments, the secondary mixture 2 is aged at between about 20° C. and about 25° C. In some embodiments, the secondary mixture 2 is aged at about 10, 15, 20, 25, or 30° C. In some embodiments, the secondary mixture 2 is aged for between about 1 hr and about 10 hrs. In some embodiments, the secondary mixture 2 is aged for between about 1 hr and about 8 hrs. In some embodiments, the secondary mixture 2 is aged for between about 1 hr and about 6.5 hrs. In some embodiments, the secondary mixture 2 is aged for between about 2.5 hrs and about 10 hrs. In some embodiments, the secondary mixture 2 is aged for between about 5 hrs and about 10 hrs. In some embodiments, the secondary mixture 2 is aged for between about 3 hrs and about 8 hrs. In some embodiments, the secondary mixture 2 is aged for between about 5 hrs and about 7 hrs. In some embodiments, the secondary mixture 2 is aged for between about 5.5 hrs and about 6.5 hrs. In some embodiments, the secondary mixture 2 is aged for about 4.0, 4,5, 5.0, 5.5, 6.0, 6.5, 7.0, 7.5, or 8.0 hrs.

In some embodiments, the crystallization step of S-7 comprises step (h) filtering the secondary mixture 2. In some embodiments, filtering provides solid crystals.

In some embodiments, the crystallization step of S-7 comprises step (i) washing the filtered crystals and/or drying under vacuum. In some embodiments, the crystallization step of S-7 comprises step (i) washing the filtered crystals. In some embodiments, the crystallization step of S-7 comprises step (i) drying under vacuum. In some embodiments, the filtered crystals are washed with the secondary solvent, e.g., as described above and herein. In some embodiments, the filtered crystals are washed between 1 and 3 times. In some embodiments, the filtered crystals are washed once. In some embodiments, the filtered crystals are washed twice. In some embodiments, the filtered crystals are washed three times. In some embodiments, a wash comprises between about 1.0 mL/g solute and about 5.0 mL/g solute of secondary solvent. In some embodiments, a wash comprises between about 2.0 mL/g solute and about 5.0 mL/g solute of secondary solvent. In some embodiments, a wash comprises between about 2.5 mL/g solute and about 5.0 mL/g solute of secondary solvent. In some embodiments, a wash comprises between about 1.0 mL/g solute and about 4.0 mL/g solute of secondary solvent. In some embodiments, a wash comprises between about 1.0 mL/g solute and about 3.5 mL/g solute of secondary solvent. In some embodiments, a wash comprises between about 2.0 mL/g solute and about 4.0 mL/g solute of secondary solvent. In some embodiments, a wash comprises between about 2.5 mL/g solute and about 3.5 mL/g solute of secondary solvent. In some embodiments, a wash comprises about 1.0, 1.5, 2.0, 2.5, 3.0, 3.5 or 4.0 mL/g solute of secondary solvent.

In some embodiments, the present invention provides a method for preparing a compound of formula I-c:

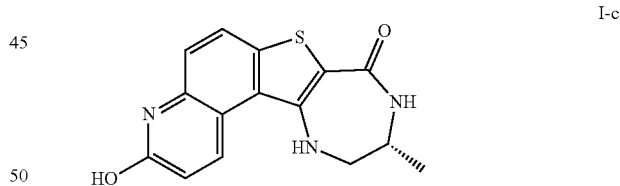

or a salt thereof,
comprising the steps of
(i) providing a compound of formula I-b

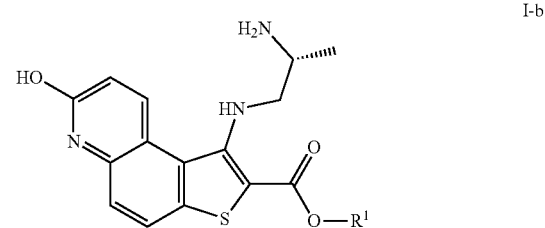

or a salt thereof, wherein R$^1$ is as described above and herein;

(ii) reacting the compound of formula I-b, or a salt thereof, with a base to thereby afford the compound of formula I-c, or a salt thereof; and (iii) crystallizing the compound of formula I-c, or a salt thereof.

In some embodiments, the present invention provides a method for preparing a compound of formula I-c:

I-c or a salt thereof,
comprising the steps of
(i) providing a compound of formula I-b

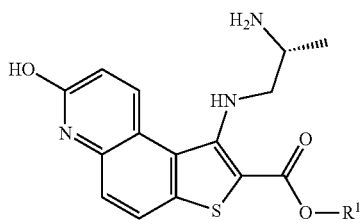

I-b or a salt thereof, where R$^1$ is as described above and herein;

(ii) reacting the compound of formula I-b, or a salt thereof, with a base to thereby afford the compound of formula I-c, or a salt thereof; and (iii) crystallizing the compound of formula I-c, or a salt thereof, wherein crystallization comprises the following steps:

(a) providing the compound of formula I-c, or a salt thereof, in a primary solvent to form a primary mixture;
(b) adding a secondary solvent to the primary mixture to form a secondary mixture 1;
(c) optionally adding a seed crystal to the secondary mixture 1;
(d) optionally aging the secondary mixture 1;
(e) optionally adding additional secondary solvent to the secondary mixture to form a secondary mixture 2;
(f) optionally agitating the secondary mixture 2;
(g) optionally aging the secondary mixture 2;
(h) filtering the secondary mixture 2; and
(i) optionally washing the filtered crystals and/or drying under vacuum.

EXEMPLARY ENUMERATED EMBODIMENTS

1. A method of preparing a compound of formula I-a:

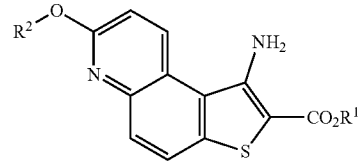

I-a or a salt thereof, wherein each of R$^1$ and R$^2$ is independently selected from optionally substituted C$_{1-6}$ aliphatic;
the method comprising:
(a) providing a compound of formula 1-4:

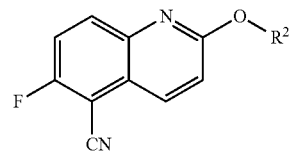

1-4 or a salt thereof; and
(b) contacting the compound of formula 1-4 with a mercaptoacetate ester of formula 1-4-a:

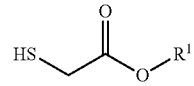

1-4-a under conditions suitable to form a compound of formula I-a, or a salt thereof.

2. The method according to embodiment 1, wherein R$^1$ is methyl.

3. The method according to embodiment 1 or embodiment 2, wherein R$^2$ is benzyl.

4. The method according to any one of embodiments 1-3, wherein the conditions suitable to form a compound of formula I-a comprise a base.

5. The method according to embodiment 4, wherein the base is an alkoxide base.

6. The method according to any one of embodiments 1-5, wherein the compound of formula 1-4, or a salt thereof, is prepared by a method comprising:
(a) providing a compound of formula 1-3:

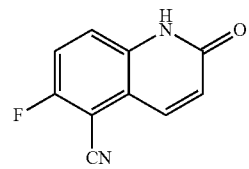

1-3 or a salt thereof; and (b) contacting the compound of formula 1-3 with a compound of formula 1-3-a:

$$R^2-X \quad\quad 1\text{-}3\text{-}a$$

under conditions suitable to form a compound of formula 1-4, or a salt thereof

7. The method according to embodiment 6, wherein $R^2$ is selected from benzyl, p-methoxybenzyl (PMB), 2,4-dimethylbenzyl, o-nitrobenzyl, p-nitrobenzyl, 2,6-dichlorobenzyl, and 3,4-dichlorobenzyl.

8. The method according to embodiment 7, wherein $R^2$ is benzyl.

9. The method according to any one of embodiments 6-8, wherein the conditions suitable to form a compound of formula 1-4 comprise a transition metal catalyst.

10. The method according to embodiment 9, wherein the transition metal catalyst is a palladium catalyst.

11. The method according to embodiment 10, wherein the conditions suitable to form a compound of formula 1-4 further comprise a phosphine ligand.

12. The method according to any one of embodiments 6-11, wherein the compound of formula 1-3, or a salt thereof, is prepared by a method comprising:

(a) providing a compound of formula 1-2:

[Structure 1-2: fluorobenzene with NH2, Br, and CN substituents]

or a salt thereof; and (b) contacting the compound of formula 1-2, or a salt thereof, with an acrylate ester of formula 1-2-a:

[Structure 1-2-a: acrylate ester with OR³]

wherein:
$R^3$ is optionally substituted $C_{1-6}$ aliphatic;
under conditions suitable to afford a compound of formula 1-3, or a salt thereof 13. The method according to embodiment 12, wherein $R^3$ is optionally substituted $C_{1-4}$ aliphatic.

14. The method according to embodiment 12 or 13, wherein $R^3$ is n-butyl.

15. The method according to any one of embodiments 12-14, wherein the conditions suitable to form a compound of formula 1-3 comprise a transition metal catalyst 16. The method according embodiment 15, wherein the transition metal catalyst is a palladium catalyst.

17. The method according to embodiment 16, wherein the conditions suitable to form a compound of formula 1-3 further comprise a phosphine ligand.

18. The method according to any one of embodiments 12-17, wherein the compound of formula 1-2, or a salt thereof, is prepared by a method comprising:

(a) providing a compound of formula 1-1:

[Structure 1-1: fluorobenzene with NH2 and CN substituents]

or a salt thereof; and (b) contacting the compound of formula 1-1, or a salt thereof, with a brominating agent under conditions suitable to afford a compound of formula 1-2, or a salt thereof 19. The method according to embodiment 18, wherein the brominating agent is selected from N-bromosuccinimide, sodium bromate/hydrobromic acid, phosphorous tribromide ($PBr_3$), bromine(I) chloride (BrCl), aluminum(III) bromide (e.g., $AlBr_3$, $Al_2Br_6$, or $AlBr_3 \cdot H_2O$), and iron(III) bromide and bromine ($FeBr_3/Br_2$).

20. The method according to embodiment 19, wherein the brominating agent is N-bromosuccinimide.

21. The method according to embodiment 19, wherein the brominating agent is sodium bromate/hydrobromic acid.

22. A compound selected from the group consisting of

[Structure 1-1]

[Structure 1-2]

[Structure 1-3]

[Structure 1-4]

or a salt thereof,
wherein $R^2$ is optionally substituted $C_{1-6}$ aliphatic.

101. A method of preparing a compound of formula I-b:

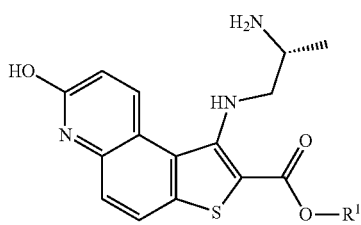

I-b or a salt thereof, wherein:
R¹ is optionally substituted $C_{1-6}$ aliphatic;
comprising the steps of:
(a) reacting a compound of formula I-a:

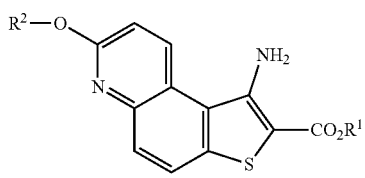

I-a or a salt thereof, wherein:
R¹ is optionally substituted $C_{1-6}$ aliphatic;
R² is optionally substituted $C_{1-6}$ aliphatic or —SO₂R$^{2a}$; and
R$^e$a is an optionally substituted $C_{1-6}$ aliphatic or aryl;
with a compound of formula 1-5:

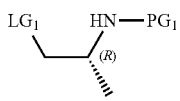

1-5 or a salt thereof, wherein:
PG¹ is a suitable nitrogen protecting group; and
LG¹ is a suitable leaving group;
under suitable reaction conditions to afford a compound of formula 1-6:

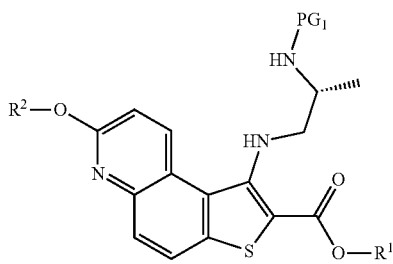

1-6 or a salt thereof; and
(b) reacting the compound of formula 1-6 under suitable reaction conditions to afford the compound of formula I-b, or a salt thereof.

102. A method for preparing a compound of formula I-b:

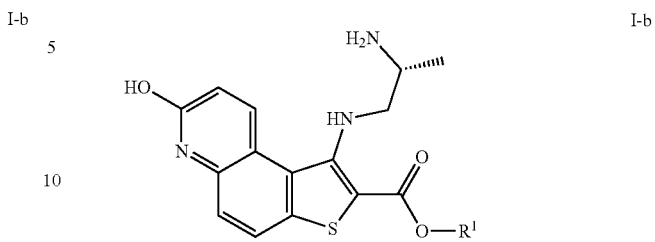

I-b or a salt thereof, wherein:
R¹ is optionally substituted $C_{1-6}$ aliphatic;
comprising the steps of:
(a) reacting a compound of formula 1-7:

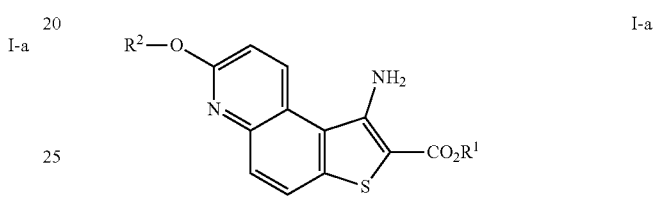

I-a or a salt thereof, wherein:
R¹ is optionally substituted $C_{1-6}$ aliphatic;
R² is optionally substituted $C_{1-6}$ aliphatic or —SO₂R$^{2a}$; and
R$^e$a is an optionally substituted $C_{1-6}$ aliphatic or aryl;
with a compound of formula 1-5-a:

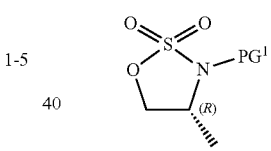

1-5-a or a salt thereof, wherein:
PG¹ is a suitable nitrogen protecting group;
under suitable reaction conditions to afford a compound of formula 1-6:

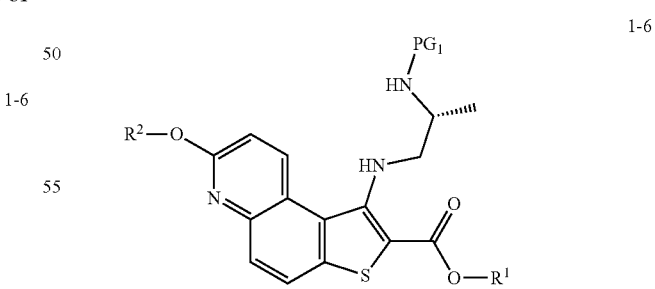

1-6 or a salt thereof; and
(b) reacting the compound of formula 1-6 under suitable reaction conditions to afford the compound of formula I-b, or a salt thereof.

103. The method of embodiment 101 or 102, wherein PG¹ is Boc.

104. The method of any one of embodiments 101-103, wherein R² is optionally substituted $C_{1-6}$ aliphatic.

105. The method of any one of embodiments 101-104, wherein R² is benzyl.

106. The method of any one of embodiments 101-103, wherein R² is —SO₂R²ᵃ.

107. The method of any one of embodiments 101-103, wherein R² is —SO₂(p-tolyl).

108. The method of any one of embodiments 101-107, wherein R¹ is methyl.

109. The method of any one of embodiments 101-108, wherein the reaction conditions to afford a compound of formula 1-6, or a salt thereof, comprise a base.

110. The method of embodiment 109, wherein the base is LiOR, NaOR, or KOR, wherein R is $C_{1-6}$ aliphatic or aryl.

111. The method of embodiment 109 or 110, wherein the base is LiOtBu.

112. The method of any one of embodiments 101-111, wherein the reaction conditions to afford a compound of formula 1-6, or a salt thereof, comprise a solvent.

113. The method of embodiment 112, wherein the solvent is N-methyl-2-pyrrolidone (NMP).

114. The method of any one of embodiments 101-113, wherein the reaction conditions to afford a compound of formula I-b, or a salt thereof, comprise an acid.

115. The method of embodiment 114, wherein the acid is a sulfonate acid.

116. The method of embodiment 114 or 115, wherein the acid is methanesulfonic acid or benzenesulfonic acid.

117. The method of any one of embodiments 101-115, wherein the reaction conditions to afford a compound of formula I-b, or a salt thereof, comprise a solvent.

118. The method of embodiment 117, wherein the solvent is MeCN.

119. The method of any one of embodiments 101-118, wherein the reaction conditions to afford a compound of formula I-b, or a salt thereof, comprise water.

120. The method of any one of embodiments 101-119, wherein a compound of formula I-b is provided as a methanesulfonic acid salt.

121. The method of any one of embodiments 101-119, wherein a compound of formula I-b is provided as a benzenesulfonic acid salt.

122. A method for preparing a compound of formula I-c:

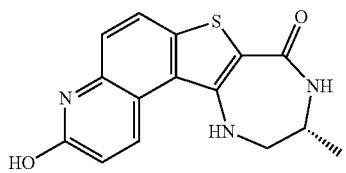

I-c or a salt thereof,
comprising the steps of
(i) providing a compound of formula I-b

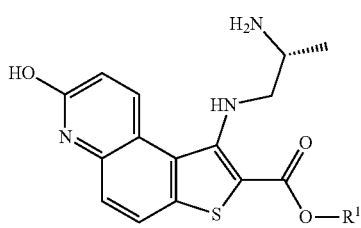

I-b or a salt thereof, where R¹ is as described above and herein;

(ii) reacting the compound of formula I-b, or a salt thereof, with a base to thereby afford the compound of formula I-c, or a salt thereof; and (iii) crystallizing the compound of formula I-c, or a salt thereof.

123. The method of embodiment 122, wherein the base is an organic base.

124. The method of embodiment 122 or 123, wherein the base is DBU.

125. The method of any one of embodiments 122-124, wherein the reaction conditions to provide a compound of formula I-b, or a salt thereof, comprise a solvent.

126. The method of embodiment 125, wherein the solvent is DMSO, dimethylacetamide (DMAc), dimethylformamide (DMF), N-methylpyrrolidone (NMP), 1,3-dimethyl-3,4,5,6-tetrahydro-2(1H)-pyrimidinone (DMPU), sulfolane, or anisole.

127. The method of embodiment 125, wherein the solvent is DMSO.

128. The method of any one of embodiments 122-127, the reaction conditions to provide a compound of formula I-b, or a salt thereof, comprise less than about 600 ppm O₂ gas.

129. The method of any one of embodiments 122-128, wherein crystallization comprises (a) providing the compound of formula I-c, or a salt thereof, in a primary solvent to form a primary mixture.

130. The method of embodiment 129, wherein the primary solvent is DMSO.

131. The method of embodiment 129 or 130, wherein the primary solvent is present at an amount of between about 4.0 mL/g solute and about 8.0 mL/g solute 132. The method of any one of embodiments 129-131, wherein the primary solvent is present at an amount of between about 4.0, 4.5, 5.0, 5.5, 6.0, 6.5, or 7.0 mL/g solute.

133. The method of any one of embodiments 129-132, wherein crystallization further comprises (b) adding a secondary solvent to the primary mixture to form a secondary mixture 1.

134. The method of embodiment 133, wherein the secondary solvent is MeCN.

135. The method of embodiment 133 or 134, wherein between about 1.0 mL/g solute and about 3.0 mL/g solute of the secondary solvent is added.

136. The method of any one of embodiments 133-135, wherein the secondary solvent is added dropwise.

137. The method of any one of embodiments 133-136, wherein the secondary solvent is added at an elevated temperature.

138. The method of embodiment 137, wherein the elevated temperature is between about 55° C. and about 65° C.

139. The method of any one of embodiments 133-138, wherein crystallization further comprises (c) adding a seed crystal to the secondary mixture 1.

140. The method of embodiment 139, wherein the seed crystal is added in an amount of between about 0.1 wt % and about 2 wt % of compound of formula I-b.

141. The method of embodiment 139 or 140, wherein the seed crystal is added in an amount of about 0.5, 0.6, 0.7, 0.8, 0.9, 1.0, 1.1, 1.2, 1.3, 1.4, or 1.5 wt % of compound of formula I-b.

142. The method of any one of embodiments 139-141, wherein the seed crystal is a compound of formula I-b, or a salt thereof.

143. The method of any one of embodiments 139-142, wherein the seed crystal is a compound of formula I-b, or a salt thereof, wherein $R^1$ is methyl.

144. The method of any one of embodiments 133-143, wherein crystallization further comprises (d) aging the secondary mixture 1.

145. The method of embodiment 145, wherein the secondary mixture 1 is aged for between about 1 hr and 4 hrs.

146. The method of embodiment 144 or 145, wherein the secondary mixture 1 is aged for about 0.5, 1.0, 1.5, 2.0, 2.5, 3.0, 3.5, or 4.0 hrs.

147. The method of any one of embodiments 144-146, wherein the secondary mixture 1 is aged at an elevated temperature.

148. The method of embodiment 147, wherein the elevated temperature is between about 55° C. and about 65° C.

149. The method of any one of embodiments 133-148, wherein crystallization further comprises (e) adding additional secondary solvent to the secondary mixture to form a secondary mixture 2.

150. The method of embodiment 149, wherein between about 1.0 mL/g solute and about 12.0 mL/g solute of secondary solvent is added.

151. The method of embodiment 149 or 150, wherein about 4.0, 4.5, 5.0, 5.5, 6.0, 6.5, 7.0, 7.5, 8.0, 8.5, or 9.0 mL/g solute of secondary solvent is added.

152. The method of any one of embodiments 149-151, wherein the additional secondary solvent is added over the course of between about 1 and 3 hrs.

153. The method of any one embodiments 149-152, wherein crystallization further comprises (f) agitating the secondary mixture 2.

154. The method of embodiment 153, wherein the secondary mixture 2 is agitated for between about 1 hr and about 4 hrs.

155. The method of embodiment 153 or 154, wherein the secondary mixture 2 is agitated at an elevated temperature.

156. The method of embodiment 155, wherein the elevated temperature is between about 55° C. and about 65° C.

157. The method of any one embodiments 149-156, wherein crystallization further comprises (g) aging the secondary mixture 2.

158. The method of embodiment 157, wherein the secondary mixture 2 is aged at between about 0° C. and about 30° C.

159. The method of embodiment 157 or 158, wherein the secondary mixture 2 is aged at about 10, 15, 20, 25, or 30° C.

160. The method of any one of embodiments 157-159, wherein the secondary mixture 2 is aged for between about 1 hr and about 10 hrs.

161. The method of any one of embodiments 157-160, wherein the secondary mixture 2 is aged for about 4,0, 4,5, 5.0, 5.5, 6.0, 6.5, 7.0, 7.5, or 8.0 hrs.

162. The method of any one of embodiments 133-161, wherein crystallization further comprises (h) filtering the secondary mixture 2.

163. The method of embodiment 162, wherein crystallization further comprises (i) washing the filtered crystals and drying under vacuum.

164. The method of embodiment 163, wherein the filtered crystals are washed with the secondary solvent.

165. The method of embodiment 163, wherein the secondary solvent is MeCN.

166. The method of any one of embodiments 163-165, wherein the filtered crystals are washed twice.

167. A compound selected from the group consisting of

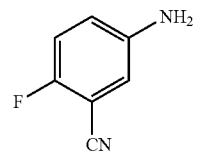

1-1

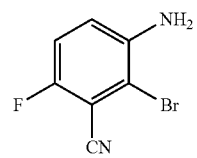

1-2

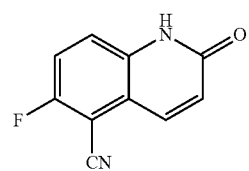

1-3

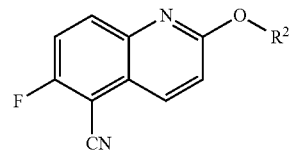

1-4

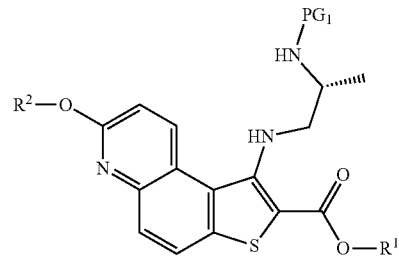

1-6

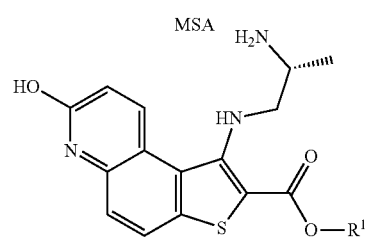

I-b or a salt thereof, wherein $R^2$ is optionally substituted $C_{1-6}$ aliphatic or $-SO_2R^{2a}$;

$R^{2a}$ is an optionally substituted $C_{1-6}$ aliphatic or aryl; and $PG^1$ is a suitable nitrogen protecting group.

168. The compound of embodiment 167, wherein $R^2$ is benzyl.

169. The compound of embodiment 167, wherein $R^2$ is $-SO_2$(p-tolyl).

170. The compound of any one of embodiments 167-169, wherein $R^1$ is methyl.

171. The compound of any one of embodiments 167-170, wherein $PG^1$ is Boc.

172. The compound of embodiment 167, selected from the group consisting of:

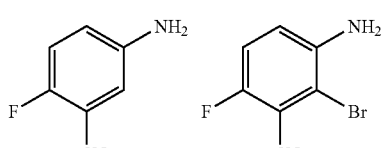
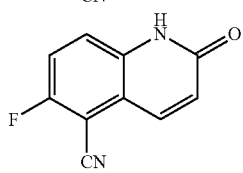
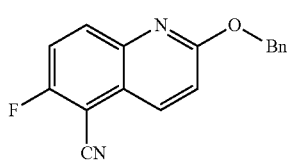
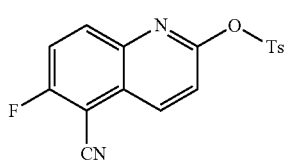
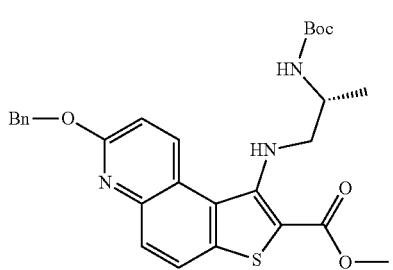
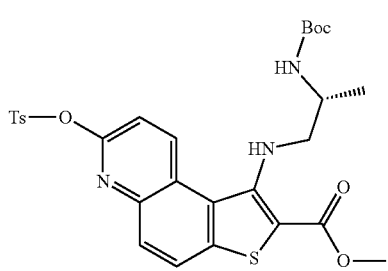
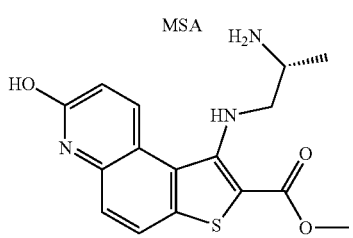

or a salt thereof.

EXAMPLES

Example 1. Synthesis of 3-Amino-2-bromo-6-fluorobenzonitrile (1-2)

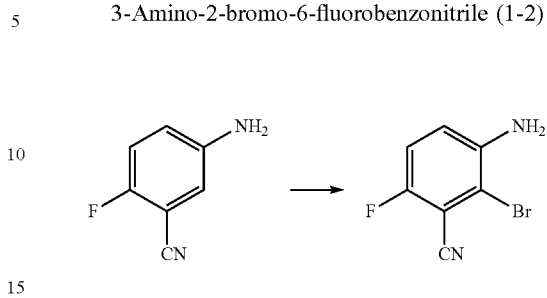

To a 250 mL round bottom flask was added 5-amino2-fluorobenzonitrile (1-1) (20.0 g, 147 mmol), followed by acetonitrile (80 mL, 1530 mmol). The reaction mixture was maintained at 20° C., and N-bromosuccinimide (26 g, 144.619 mmol) was added in portions. The reaction was allowed to warm to room temperature and stirred for 30 minutes. After 30 minutes, 80 mL water was charged to the reaction mixture over about 1 hr. The reaction mixture was filtered and washed with 30 mL (1.5 vol ) of 3:1 water:ACN solvent mixture to afford a brown cake. The solids were collected and dried under vacuum at 50° C. to afford 25 g of 3-amino-2-bromo-6-fluorobenzonitrile (1-2) as a brown solid (79% yield).

Example 2. Synthesis of 3-Amino-2-bromo-6-fluorobenzonitrile (1-2)

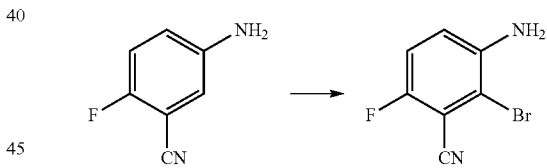

To a 2L round bottom flask was added 5-amino-2-fluorobenzonitrile (1-1) (50 g, 356.3 mmol). Acetonitrile (500 mL, 10.0 mL/g) and the mixture was allowed to stir at room temperature for 5 minutes. Sodium bromate (18.82 g, 0.35 eq.) and water (100 mL) were added and the reaction was stirred for 5 minutes. Hydrobromic acid in water (48%, 42 mL, 1.050 eq.) was added via an addition funnel over a 5 minute period. A slight exotherm was observed. The reaction was allowed to stir for about 30 minutes. The product precipitated as large needle crystals. An aqueous solution of sodium thiosulfate pentahydrate (17.68 g, 0.2 eq. in 400 mL water) was added to the reaction mixture via an addition funnel over about 20 minutes. The reaction mixture was allowed to stir for another 30 minutes, after which the mixture was filtered, and the filter cake was washed with 2:1 acetonitrile:water (2×100mL) and then deionized water (2×100 mL). The solids were dried under vacuum at 50° C. overnight to afford 50.2 g of 3-amino-2-bromo-6-fluorobenzonitrile as a gray solid (65.5% yield).

Example 3. Synthesis of 6-Fluoro-2-oxo-1,2-dihydroquinoline-5-carbonitrile (1-3)

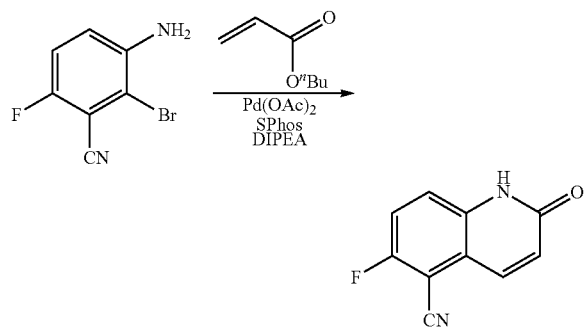

To a 250 mL round bottom flask was added 3-amino-2-bromo-6-fluorobenzonitrile (1-2) (12.0 g, 55.0 mmol) and toluene (96 mL) that was pre-sparged with $N_2$. The reaction mixture was sparged with $N_2$ at room temperature for at least 20 minutes, and then Pd(OAc)2 (376 mg, 1.675 mmol) and 2-dicyclohexylphosphino-2',6'-dimethoxybiphenyl (764 mg, 1.84 mmol) were added. The reaction mixture was again sparged with $N_2$ for an additional 10 minutes, and then butyl acrylate (16 mL; 112 mmol) and N,N-diisopropylethylamine (11.7 mL, 66.9 mmol) were added. The reaction mixture was sparged with $N_2$ for an additional 5 minutes and then heated to 105° C. for 21 hours. The reaction was allowed to cool to 80° C. and HCl (5.5 M) in isopropanol (35 mL) was added in one portion and the reaction was stirred overnight (~21 h) at 75-80° C. The reaction was quenched by the addition of saturated $NaHCO_3$ (~90 mL, 7.5 volumes) over about 5 minutes at 80 ° C. The reaction was allowed to stir for at least 10 minutes at 60° C., and then cooled to 20° C. and allowed to age for 2 hours. The solids were filtered and washed with 2 volumes (24 mL) of 1:1 isopropanol:water. The solids were collected and dried at 50° C. overnight under vacuum to afford 7.3 g of 6-fluoro-2-oxo-1,2-dihydroquinoline-5-carbonitrile as a brown solid (70% yield).

Example 4. Synthesis of 6-Fluoro-2-oxo-1,2-dihydroquinoline-5-carbonitrile (1-3)

To a 100 mL easy max reactor with air condenser and temperature probe was flushed with nitrogen. To the reactor was charged 3-amino-2-bromo-6-fluorobenzonitrile (5.0 g, 23.25 mmol, 1 equiv, 1×Wt) followed by degassed toluene (40 mL, 8×Vol, 6.94×Wt). The dark brown suspension was agitated at 300 RPM under nitrogen. To the reactor was charged N-butyl acrylate (3.5 mL, 24.42 mmol, 1.05 eq, 0.7×Vol, 0.63×Wt) followed by N,N,-diisopropylethylamine (4.9 mL, 28.16 mmol, 1.2 eq, 0.98×Vol, 0.73×Wt). The agitating suspension was then sparged with nitrogen for 15 min. Pd(Amphos)Cl$_2$ was then charged into the reactor (0.49 g, 0.692 mmol, 0.03 eq, 0.1×Wt). The reaction was sparged with nitrogen for 15 min. The reaction was a dark brown suspension. The reaction was heated to 105° C. At that temperature the reaction was a dark brown/black solution. After 2 hours, brown precipitate started to form and the reactions was a suspension. A 500 µL sample was taken and diluted to 40 ml with ACN. UPLC analysis showed the ratio of cyclized product : Heck product was 75:25. The reaction was heated for an additional 14 hours and analyzed again with the same sampling procedure. UPLC analysis showed the ratio of cyclized product : Heck product was 91:9. The reaction was a light brown suspension. The reaction was cooled to 22° C. and to the reaction was charged 40 mL of ACN (8×Vol, 6.3×Wt). The reaction was heated to 80° C. for 1 hour and then cooled to 5° C. The reaction was filtered through a disposable funnel and the reactor and cake was washed with toluene (10 mL, 2×Vol 1.7×Wt) and pulled to dryness. The cake was dried in a vacuum oven at 40° C. for 2 hours.

3.14 g of 6-fluoro-2-oxo-1,2-dihydroquinoline-5-carbonitrile was isolated as a light brown powder (71.7% isolated yield; 4.38 g Theoretical Yield), LCAP: 99.79%. 1H QNMR: 88% wt purity, Corrected Yield: 2.76 g, 63.1%.

Example 5. Synthesis of 2-(Benzyloxy)-6-fluoroquinoline-5-carbonitrile

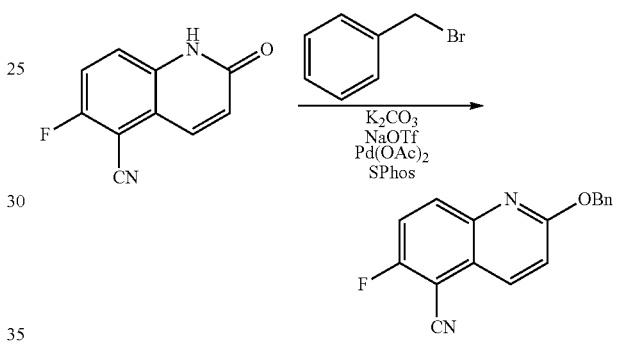

To a 100 mL reactor was added 6-fluoro-2-oxo-1,2-dihydroquinoline-5-carbonitrile (5 g, 1.0 eq.), K$_2$CO$_3$ (3.89 g, 1.1 eq.), NaOTf (0.45 g, 0.1 eq.), and toluene (25 mL, 5 volumes), and benzyl bromide (6.56 g, 1.5 eq.). The reaction mixture was stirred and sparged with N$_2$ three times. Pd(OAc)$_2$ (287 mg, 0.05 eq.) and SPhos (589 mg, 0.055 eq.) were added, followed by an additional 5 volumes (25 mL) of toluene. The reaction mixture was again sparged with N$_2$ for an additional five times. The reaction was then heated to 100° C. for 16 h. The reaction was cooled to 75° C. and the solids were filtered and washed with hot toluene (3×5 volumes at 75° C.). The filtrate was concentrated to about 25 mL (5 volumes), cooled to 0° C., and aged for about 30 minutes. The precipitate was filtered and washed with 3×10 mL cold toluene and dried under vacuum at 50° C. overnight to yield 5.87 g of 2-(benzyloxy)-6-fluoroquinoline-5-carbonitrile as an off-white solid (76.8% yield).

Example 6. Synthesis of Methyl 1-amino-7-(benzyloxy)thieno[3,2-f]quinoline-2-carboxylate

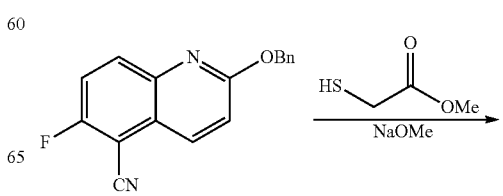

-continued

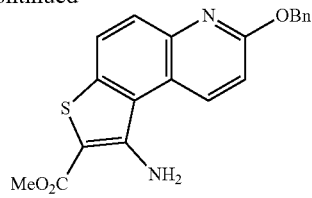

To a 250 mL round bottom flask was charged 2-(benzyloxy)-6-fluoroquinoline-5-carbonitrile (5.0 g, 16.8 mmol) and tetrahydrofuran (50 mL, 10 mL/g) and the mixture was stirred for 5 minutes. Methyl thioglycolate (2.67 g, 25.1 mmol, 1.5 eq.) was added, followed by sodium methoxide (25 mass %) in methanol (4.71 g, 4.98 mL, 21.8 mmol, 1.3 eq.). A slight exotherm was observed, and the reaction was allowed to stir at room temperature for about 2 h. Deionized water (0.5 volume; about 0.25 mL) was added and the reaction was aged for about 30 minutes. Another 0.5 volume of deionized water was added and the reaction was allowed to stir for another 30 minutes. A slurry formed, another 6 volumes of water (30 mL) were added over about 20 minutes, and the slurry was aged for an additional 30 minutes. The precipitate was filtered and washed with 2:1 water/THF (4×20 mL). The solids were collected and dried under vacuum at 50° C. to yield 5.50 g of methyl 1-amino-7-(benzyloxy)thieno[3,2-f]quinoline-2-carboxylate as a light yellow solid (87.7% yield).

Example 7. Synthesis of Methyl (R)-1-((2-aminopropyl)amino)-7-hydroxythieno[3,2-f]quinoline-2-carboxylate Methanesulfonate

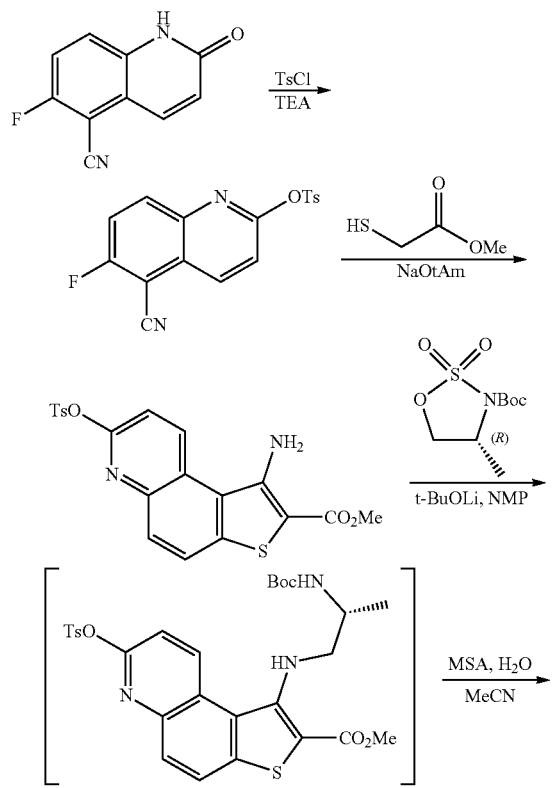

-continued

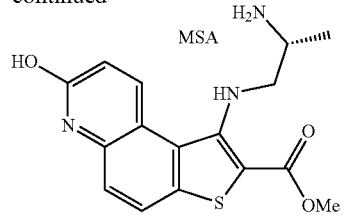

5-Cyano-6-fluoroquinolin-2-yl 4-methylbenzenesulfonate. To a slurry of 6-fluoro-2-oxo-1H-quinoline-5-carbonitrile (5.00 g, 26.6 mmol, 1.0 equiv) in THF (100 mL) was added 4-dimethylaminopyridine (0.117 g, 0.035 equiv., 0.930 mmol) at ambient temperature. p-Toluenesulfonyl chloride (6.01 g, 1.15 equiv., 30.6 mmol) was then added, followed by triethylamine (4.81 mL, 1.3 equiv., 34.5 mmol). The mixture was heated to 55° C. until the starting material was consumed, as monitored by HPLC analysis. The reaction mixture was then cooled to 20° C. and filtered. The reactor was rinsed with THF (7.5 mL×2), and the rinses were applied to the cake washed. The resulting filtrates were combined and concentrated under vacuum at 35-50° C. to ~35 mL. Heptane (60 mL) was added. The batch was concentrated to ~75 mL at 30-50° C., then cooled to 20° C. The resulting slurry was mixed for 1 h prior to filtration. The filter cake was washed with a mixture of THF and heptane (¼, v/v, 15 mL ×2), dried under vacuum at 50° C. to constant weight, affording 8.10 g of 5-cyano-6-fluoroquinolin-2-yl 4-methylbenzenesulfonate as pale solids in 89% yield. $1_H$ NMR (400 MHz, chloroform-d) δ 8.49 (d, J=8.9 Hz, 1H), 8.13 (dd, J=9.4, 5.1 Hz, 1H), 8.01 (d, J=8.3 Hz, 2H), 7.58 (t, J=8.9 Hz, 1H), 7.39 (d, J=8.7 Hz, 3H), 2.47 (s, 3H). $13_C$ NMR (101 MHz, chloroform-d) δ 162.9 (d, J=264 Hz, 1C), 156.0 (d, J=3.0 Hz), 145.8, 142.4, 137.5(d, J=5.8 Hz), 136.3(d, J=9.5 Hz), 133.4, 129.7, 128.9, 126.6 (d, J=3.0 Hz), 120.0 (d, J=24.2 Hz), 117.4, 111.7, 96.5 (d, J=16.9 Hz), 21.7. LCMS m/z (M+H)$^+$:343.

Methyl 1-amino-7-(tosyloxy)thieno[3,2-f]quinoline-2-carboxylate. To a solution of 5-cyano-6-fluoroquinolin-2-yl 4-methylbenzenesulfonate (5.00 g, 13.8 mmol, 1.0 equiv) in THF (100 mL) was added methylthioglycolate (1.36 mL, 1.10 equiv., 15.1 mmol) at 0° C. Sodium t-pentoxide in THF (1.70 mL, 1.4 equiv., 19.3 mmol, 2.50 mol/L) was then added over a period of 5-10 min at below 15° C. After the starting material was consumed, toluene (20 mL) was added into the reaction mixture, followed by 10% aqs K$_2$HPO$_4$ solution (50 mL). The batch was then warmed to 20° C. and mixed for 5 min prior to a phase split. The aqueous layer was removed. The organic phase was again washed with 10% aqs K$_2$HPO$_4$ solution (50 mL), and concentrated under vacuum at 35° C. to ~50 mL. The resulting mixture was cooled to 20° C., and toluene (25 mL) was added over a period of 5 min. The batch was mixed for 1 h prior to filtration. The reactor was rinsed with a mixture of THF/toluene (1:9 v/v, 10 mL), and the rinse was applied to the cake wash. The cake was washed with a mixture of THF and toluene (1:9 v/v, 10 mL), and dried under vacuum at 50° C. to constant weight, affording 4.90 g of methyl 1-amino-7-(tosyloxy)thieno[3,2-f]quinoline-2-carboxylate as yellow solids in 82% yield. $^1$H NMR (400 MHz, chloroform-d) δ 8.83 (d, J=8.9 Hz, 1H), 8.02 (d, J=8.2 Hz, 2H), 7.78 (d, J=8.9 Hz, 1H), 7.69 (d, J=9.0 Hz, 1H), 7.41-7.34 (m, J=8.3 Hz, 2H), 7.31-7.23 (m, 1H), 6.05 (br s, 2H), 3.93 (s, 3H), 2.46 (s, 3H). $^{13}$C NMR (101 MHz, chloroform-d) δ 165.5, 154.0, 151.2, 145.4, 145.4, 139.5, 133.9, 133.8, 129.6, 128.9, 128.6, 125.6, 124.7, 124.0, 114.0, 103.9, 51.8, 21.7. LCMS m/z (M+H)+: 429.

Methyl (R)-1-((2-aminopropyl)amino)-7-hydroxythieno[3,2-f]quinoline-2-carboxylate methanesulfate. To a solution of methyl 1-amino-7-(tosyloxy)thieno[3,2-f]quinoline-2-carboxylate (2.00 g, 4.67 mmol, 1.0 equiv) in NMP (8 mL) was add 2-MeTHF (8 mL). The mixture was cooled to between −5 to 0° C. Tert-butyl (R)-4-methyl-1,2,3-oxathiazolidine-3-carboxylate 2,2-dioxide (1.22 g, 1.10 equiv., 5.13 mmol) was then added, immediately followed by lithium t-butoxide in THF (2.55 mL, 1.20 equiv., 5.60 mmol, 2.20 mol/L) at below 5° C. After the starting material was consumed, acetic acid (0.334 mL, 1.25 equiv., 5.83 mmol) was added to quench the reaction. The resulting reaction mixture was diluted with 2-MeTHF (20 mL) and warmed to 20° C. The batch was then washed with aqs. 5% NaH2PO4 solution (20 mL), water (20 mL), and finally aqs. 5% NaH2PO4 solution (20mL). The resulting organic phase was concentrated, and solvent-exchanged to MeCN. The batch volume was adjusted to ~25 mL, and methanesulfonic acid (0.92 mL, 3 equiv., 14.0 mmol) was added followed by water (1.26 mL, 15 equiv., 70.0 mmol). The batch was heated at 65° C. until the reaction completed. The mixture was then cooled to 20° C., and stirred for 1 h prior to filtration. The resulting filter cake was washed with MeCN (5 mL ×2) and dried under vacuum at 35° C. to constant weight, affording 1.20 g of the product as orange solids in 60% yield. $^1$H NMR (400 MHz, DMSO-$d_6$) δ 12.13 (br s, 1H), 8.67 (d, J=9.9 Hz, 1H), 8.07 (d, J=8.8 Hz, 1H), 7.91 (br s, 3H), 7.54 (d, J=8.8 Hz, 1H), 6.70 (d, J=9.9 Hz, 1H), 6.22 (br s, 1H), 3.89 (s, 3H), 3.44-3.26 (m, 2H), 3.17-3.01 (m, 1H), 2.35 (s, 3H), 1.26 (d, J=6.4 Hz, 3H). $^{13}$C NMR (101 MHz, DMSO-$d_6$) δ 164.1, 161.2, 151.0, 138.1, 135.6, 133.8, 128.1, 125.8, 125.5, 122.0, 117.7, 114.5, 114.3, 52.4, 52.2, 46.8, 16.4. LCMS m/z (M+H)+:332.

Example 8: Synthesis of (R)-3-Hydroxy-10-methyl-9,10,11,12-tetrahydro-8H-[1,4] diazepino[5',6':4,5]thieno[3,2-f] quinolin-8-one

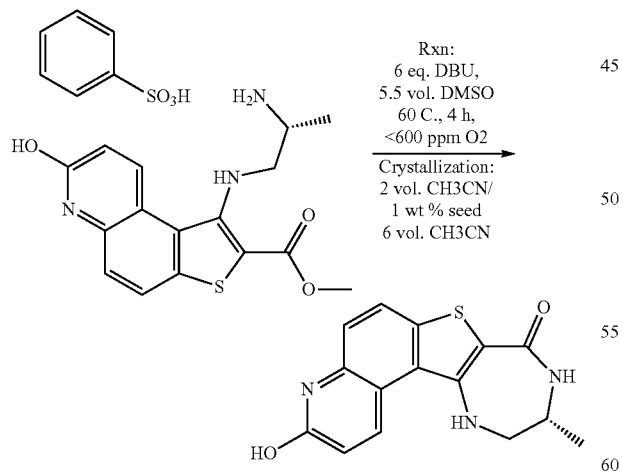

To a 250 mL Chemglass reactor equipped with overhead stirring was charged with methyl (R)-1-((2-aminopropyl)amino)-7-hydroxythieno[3,2-f] quinoline-2-carboxylate benzenesulfonate (15.0 g, limiting reagent). To the reactor was charged DMSO (100mL, 5.0 mL/g), which was degassed with nitrogen. The reaction vessel was inerted with nitrogen to <600 ppm O2, which was monitored by a Teledyne O2 monitor system. The reaction mixture was heated to 60° C., and DBU (4.6mL, 1.0 equiv.) was charged dropwise over no less than 1 h. Subsequently, DBU (23mL, 5.0 equiv.) was charged over 10 minutes, followed by DMSO (7.5 mL, 0.50 mL/g). The reaction mixture was aged at 60° C. over 4 h until the starting material was consumed by HPLC analysis. Next, ACN (30mL, 2.0 mL/g) was added dropwise at 60° C. The reaction mixture was seeded with (R)-3-hydroxy-10-methyl-9,10,11,12-tetrahydro-8H-[1,4] diazepino[5',6':4,5]thieno[3,2-f]quinolin-8-one (0.150 g, 0.010 equiv.) and aged for 2 h at 60° C. Additional ACN (90mL, 6.0 mL/g) was charged to the slurry over 2 h. After agitating the slurry at 60° C. for 2 h, the mixture was cooled to 20° C. and aged for 6 h. The slurry was filtered and washed twice with ACN (45mL, 3.0 mL/g). The wet cake was collected and dried under vacuum at 50° C. until reaching constant weight, affording 7.8 g (85% yield) of the product as a yellow solid. All spectral data are in accordance with the literature, e.g., WO 2016/044463.

The invention claimed is:

1. A method of preparing a compound of formula I-a:

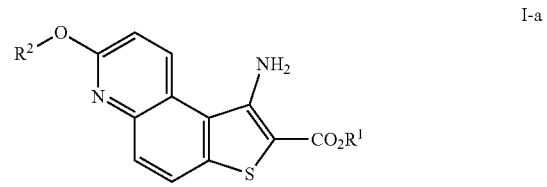

or a salt thereof, wherein $R^1$ is optionally substituted $C_{1-6}$ aliphatic;

$R^2$ is selected from optionally substituted $C_{1-6}$ aliphatic and —$SO_2R^{2a}$; and wherein $R^{2a}$ is an optionally substituted $C_{1-6}$ aliphatic or aryl;

the method comprising:
(a) providing a compound of formula 1-4:

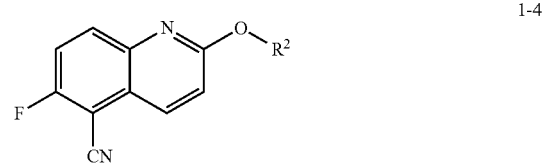

or a salt thereof; and
(b) contacting the compound of formula 1-4 with a mercaptoacetate ester of formula 1-4-a:

under conditions suitable to form a compound of formula I-a, or a salt thereof.

2. The method according to claim 1, wherein $R^1$ is methyl.

3. The method according to claim 1, wherein $R^2$ is benzyl or tosyl.

4. The method according to claim 1, wherein the compound of formula 1-4, or a salt thereof, is prepared by a method comprising:
(a) providing a compound of formula 1-3:

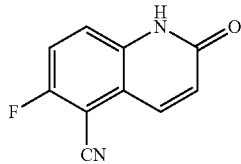

1-3 or a salt thereof; and
(b) contacting the compound of formula 1-3 with a compound of formula 1-3-a:

R²–X    1-3-a wherein:
X is a suitable leaving group;
under conditions suitable to form a compound of formula 1-4, or a salt thereof.

5. The method according to claim 4, wherein R² is benzyl or tosyl.

6. The method according to claim 4, wherein the compound of formula 1-3, or a salt thereof, is prepared by a method comprising:
(a) providing a compound of formula 1-2:

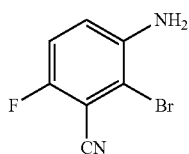

1-2 or a salt thereof; and
(b) contacting the compound of formula 1-2, or a salt thereof, with an acrylate ester of formula 1-2-a:

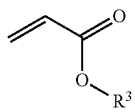

1-2-a wherein:
R³ is optionally substituted $C_{1-6}$ aliphatic;
under conditions suitable to afford a compound of formula 1-3, or a salt thereof.

7. The method according to claim 6, wherein the compound of formula 1-2, or a salt thereof, is prepared by a method comprising:
(a) providing a compound of formula 1-1:

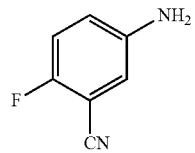

1-1 or a salt thereof, and
(b) contacting the compound of formula 1-1, or a salt thereof, with a brominating agent under conditions suitable to afford a compound of formula 1-2, or a salt thereof.

8. The method according to claim 2, wherein R² is benzyl.

9. The method according to claim 2, wherein R² is tosyl.

10. The method according to claim 7, wherein the brominating agent is N-bromosuccinimide or sodium bromate/hydrobromic acid.

11. The method according to claim 9, wherein the conditions suitable to form a compound of formula 1-a, or a salt thereof, comprise a base.

12. The method according to claim 4, wherein R¹ is methyl.

13. The method according to claim 12, wherein R² is benzyl.

14. The method according to claim 12, wherein R² is tosyl.

15. The method according to claim 14, wherein the conditions suitable to form a compound of formula 1-4, or a salt thereof, comprise a palladium catalyst.

16. The method according to claim 6, wherein R³ is n-butyl.

17. The method according to claim 6, wherein the conditions suitable to form a compound of formula 1-4, or a salt thereof, comprise a palladium catalyst.

18. The method according to claim 6, wherein R¹ is methyl.

19. The method according to claim 18, wherein R² is benzyl or tosyl.

20. The method according to claim 7, wherein R² is benzyl or tosyl.

* * * * *